United States Patent [19]

Legoux et al.

[11] Patent Number: 5,480,800
[45] Date of Patent: Jan. 2, 1996

[54] DNA FRAGMENT CARRYING THE GENE ENCODING THE ENZYME FOR FRAGMENTING N-ACETYLHEPAROSAN AND THE ADJACENT SEQUENCES PERMITTING ITS EXPRESSION, RECOMBINANT ENZYME INTENDED FOR FRAGMENTING N-ACETYLHEPAROSAN AND ITS USE

[75] Inventors: Richard Legoux, Le Saget; Philippe Lelong; Marc L. V. Salomé, both of Castanet Tolosan, all of France

[73] Assignee: Sanofi, Paris, France

[21] Appl. No.: 291,896

[22] Filed: Aug. 17, 1994

[30] Foreign Application Priority Data

Aug. 17, 1993 [FR] France ................................. 93 10050

[51] Int. Cl.⁶ ............................. C12N 15/70; C12N 9/24; C12N 15/63; C12N 1/21
[52] U.S. Cl. ................. 435/252.33; 435/200; 435/320.1; 536/23.2
[58] Field of Search ..................... 536/23.2; 435/252.33, 435/320.1, 200

[56] References Cited

FOREIGN PATENT DOCUMENTS 0489647  6/1992  European Pat. Off. .

OTHER PUBLICATIONS

Dhirendra S. Gupta et al., "Enzymatic degradation of the capsular K5–antigen of *E. coli* by coliphage K5", FEMS Microbiology Letters, vol. 16, No. 1, Jan. 1983, pp. 13–17.

*Primary Examiner*—Robert A. Wax
*Assistant Examiner*—Kawai Lau
*Attorney, Agent, or Firm*—Jacobson, Price, Holman & Stern

[57] ABSTRACT

The invention relates to a DNA fragment of SEQ ID NO: 1 herein and encoding the SEQ ID NO: 2 peptide sequence herein. This DNA sequence carries the gene encoding the enzyme for fragmenting N-acetylheparosan and the adjacent sequences permitting its expression. The invention also relates to an enzyme intended for fragmenting N-acetylheparosan derived from this gene and the processes for fragmenting high molecular mass N-acetylheparosan using this enzyme.

7 Claims, 7 Drawing Sheets

FIG. 1A

```
GATCCCGGAG  TAATTTCATC  AAGTGCGATC  CCTCCACCAG  TGACCTGACG
                                                              50
CTAGGGCCTC  ATTAAAGTAG  TTCACGCTAG  GGAGGTGGTC  ACTGGACTGC

CCTCCCGGCG  TGTGAATCCT  TTCGGTAAAT  CCCTCTTCCA  GTGGATAGTG
                                                              100
GGAGGGCCGC  ACACTTAGGA  AAGCCATTTA  GGGAGAAGGT  CACCTATCAC

ATACTGCTGC  ATCTTAATCT  TCTCCATGCA  ATAACTGTAT  ATTTATACAG
                                                              150
TATGACGACG  TAGAATTAGA  AGAGGTACGT  TATTGACATA  TAAATATGTC

TAGCAAATAA  TTTGTTTGCT  ATCCAGCACG  TTTTGCAAAT  TACCTGAAAG
                                                              200
ATCGTTTATT  AAACAAACGA  TAGGTCGTGC  AAAACGTTTA  ATGGACTTTC

GTAATATCTA  TTCATATTCA  CAGTCTTTCT  ATCCATATAT  GGTTTTTTGG
                                                              250
CATTTATAGAT AAGTATAAGT  GTCAGAAAGA  TAGGTATATA  CCAAAAAACC

GTAATAGAAT  AACCAGATAT  GCGGCGCAAC  GGGTGCTGCG  ACTATCTGGA
                                                              300
CATTATCTTA  TTGGTCTATA  CGCCGCGTTG  CCCACGACGC  TGATAGACCT
```

```
GA  TTT  AAC  ATG  ACG  GCT  TCA  ACC  GAA  GTT  GAC  CAC  AAC  GAA  TAC
                                                                              344
CT  AAA  TTG  TAC  TGC  CGA  AGT  TGG  CTT  CAA  CTG  GTG  TTG  CTT  ATG
            Met  Thr  Val  Ser  Thr  Glu  Val  Asp  His  Asn  Glu  Tyr
             1              5                        10

ACA  GGT  AAC  GGC  GTT  ACG  ACA  TCA  TTT  CCG  TAT  ACC  TTC  CGT  ATT
                                                                              389
TGT  CCA  TTG  CCG  CAA  TGC  TGT  AGT  AAA  GGC  ATA  TGG  AAG  GCA  TAA
Thr  Gly  Asn  Gly  Val  Thr  Thr  Ser  Phe  Pro  Tyr  Thr  Phe  Arg  Ile
                15                        20                        25

TTC  AAA  AAA  TCC  GAC  CTG  GTT  GTT  CAG  GTG  TCT  GAC  CTT  AAC  GGT
                                                                              434
AAG  TTT  TTT  AGG  CTG  GAC  CAA  CAA  GTC  CAC  AGA  CTG  GAA  TTG  CCA
Phe  Lys  Lys  Ser  Asp  Leu  Val  Val  Gln  Val  Ser  Asp  Leu  Asn  Gly
                30                        35                        40

AAC  GTT  ACA  AAA  CTA  GTG  CTG  GAT  GCT  GGT  TAT  ACG  GTA  ACA  CGG
                                                                              479
TTG  CAA  TGT  TTT  GAT  CAC  GAC  CTA  CGA  CCA  ATA  TGC  CAT  TGT  CCC
Asn  Val  Thr  Lys  Leu  Val  Leu  Asp  Ala  Gly  Tyr  Thr  Val  Thr  Gly
                45                        50                        55

GCG  GGA  ACT  TAT  AGT  GGC  GGT  GCA  GTG  GTT  CTT  CCG  TCG  CCG  CTT
                                                                              524
CGC  CCT  TGA  ATA  TCA  CCG  CCA  CGT  CAC  CAA  GAA  GGC  AGC  GGC  GAA
Ala  Gly  Thr  Tyr  Ser  Gly  Gly  Ala  Val  Val  Leu  Pro  Ser  Pro  Leu
                60                        65                        70
```

FIG. 1B

```
GCT GCT GGC TGG CGA ATC ACG ATA GAG CGT GTG CTT GAT GTG GTG
--- --- --- --- --- --- --- --- --- --- --- --- --- --- --- 569
CGA CGA CCG ACC GCT TAG TGC TAT CTC GCA CAC GAA CTA CAC CAC
Ala Ala Gly Trp Arg Ile Thr Ile Glu Arg Val Leu Asp Val Val
         75              80              85

CAG GAG ACT GAT CTT CGC AAT CAG GGA AAA TTT TTC CCC GAA GTT
--- --- --- --- --- --- --- --- --- --- --- --- --- --- --- 614
GTC CTC TGA CTA GAA GCG TTA GTC CCT TTT AAA AAG GGG CTT CAA
Gln Glu Thr Asp Leu Arg Asn Gln Gly Lys Phe Phe Pro Glu Val
         90              95             100

CAT GAG GAT GCA TTT GAC TAC CTG ACG ATG CTG ATC CAG CGA TGT
--- --- --- --- --- --- --- --- --- --- --- --- --- --- --- 659
GTA CTC CTA CGT AAA CTG ATG GAC TGC TAC GAC TAG GTC GCT ACA
His Glu Asp Ala Phe Asp Tyr Leu Thr Met Leu Ile Gln Arg Cys
        105             110             115

TTT GGG TGG TTC AGA CGT GCA TTG ATG AAA CCA TCT TTG CTT GAT
--- --- --- --- --- --- --- --- --- --- --- --- --- --- --- 704
AAA CCC ACC AAG TCT GCA CGT AAC TAC TTT GGT AGA AAC GAA CTA
Phe Gly Trp Phe Arg Arg Ala Leu Met Lys Pro Ser Leu Leu Ala
        120             125             130

AAA TAT TAC GAT GCA AAG CAA AAC AGA ATA TCT AAC CTT GCC GAT
--- --- --- --- --- --- --- --- --- --- --- --- --- --- --- 749
ATA TTT ATG CTA CGT TTC GTT TTG TCT TAT AGA TTG GAA CGG CTA
Lys Tyr Tyr Asp Ala Lys Gln Asn Arg Ile Ser Asn Leu Ala Asp
        135             140             145

CCA TCA CTT GAG CAG GAC GCT GTA AAT AAT CGC TCA ATG CGT AAT
--- --- --- --- --- --- --- --- --- --- --- --- --- --- --- 794
GGT AGT GAA CTC GTC CTG CGA CAT TTA TTA GCG AGT TAC GCA TTA
Pro Ser Leu Glu Gln Asp Ala Val Asn Asn Arg Ser Met Arg Asn
        150             155             160

TAT GTC GAT GCT GCA ATC GCC GGA GTT ATT GGT GGT TTT GGT TGG
--- --- --- --- --- --- --- --- --- --- --- --- --- --- --- 839
ATA CAG CTA CGA CGT TAG CGG CCT CAA TAA CCA CCA AAA CCA ACC
Tyr Val Asp Ala Ala Ile Ala Gly Val Ile Gly Gly Phe Gly Trp
        165             170             175

TTT ATT CAG TAT GGT TCT GGA GCG GTA TAC AGA ACG TTC CAG GAT
--- --- --- --- --- --- --- --- --- --- --- --- --- --- --- 884
AAA TAA GTC ATA CCA AGA CCT CGC CAT ATG TCT TGC AAG GTC CTA
Phe Ile Gln Tyr Gly Ser Gly Ala Val Tyr Arg Thr Phe Gln Asp
        180             185             190

AAG ATG CGT GAT GGT GTC AGC ATT AAG GAT TTT GGA GCT CAA AAT
--- --- --- --- --- --- --- --- --- --- --- --- --- --- --- 929
TTC TAC GCA CTA CCA CAG TCG TAA TTC CTA AAA CCT CGA GTT TTA
Lys Met Arg Asp Gly Val Ser Ile Lys Asp Phe Gly Ala Gln Asn
        195             200             205

GGA ATC TTA ATT GAT AAC AAG GAT GCT TTT ACA AAA TCA TTA CAT
--- --- --- --- --- --- --- --- --- --- --- --- --- --- --- 974
CCT TAG AAT TTA CTA TTG TTC CTA CGA AAA TGT TTT AGT AAT GTA
Gly Ile Leu Asn Asp Asn Lys Asp Ala Phe Thr Lys Ser Leu His
        210             215             220
```

FIG. 1C

```
TCG TTT AGC AGT GTT TTT GTT CCG GAA GGG GTA TTC AAT ACA TCT
                                                               — 1019
AGC AAA TCG TCA CAA AAA CAA GGC CTT CCC CAT AAG TTA TGT AGA
Ser Phe Ser Ser Gln Lys Gln Gly Leu Pro His Lys Leu Cys Arg
        225                 230                 235

TTA GTT TCT CTT TCA CGT TGT GGC TTG TAC GGA ACA GGT GGG GGA
                                                               — 1064
AAT CAA AGA GAA AGT GCA ACA CCG AAC ATG CCT TGT CCA CCC CCT
Leu Val Ser Leu Ser Arg Cys Gly Leu Tyr Gly Thr Gly Gly Gly
        240                 245                 250

ACG ATA AAA CAG TAT GAC AGA GAT GGT AAT CAT CTG GTT TTT AAC
                                                               — 1109
TGC TAT TTT GCT ATA CTG TCT CTA CCA TTA GTA GAC CAA AAA TTG
Thr Ile Lys Gln Tyr Asp Arg Asp Gly Asn His Leu Val Phe Asn
        255                 260                 265

ATG CCC GAT GGT GGC ATG CTT AGT ACG CTA ACA ATT ATG GGA AAT
                                                               — 1154
TAC GGG CTA CCA CCG TAC GAA TCA TGC GAT TGT AAT TAC CCT TTA
Met Pro Asp Gly Gly Met Leu Ser Thr Leu Thr Ile Met Gly Asn
        270                 275                 280

AAA TCA GAT GAT AGT GTG CAG GGA CAC CAG GTG TCA TTT TCA GGT
                                                               — 1199
TTT AGT CTA CTA TCA CAC GTC CCT GTG GTC CAC AGT AAA AGT CCA
Lys Ser Asp Asp Ser Val Gln Gly His Gln Val Ser Phe Ser Gly
        285                 290                 295

GGC CAT GAT GTA TCG GTT AAA AAT ATC AGA TTT ACA AAT ACG CGA
                                                               — 1244
CCG GTA CTA CAT AGC CAA TTT TTA TAG TCT AAA TGT TTA TGC GCT
Gly His Asp Val Ser Val Lys Asn Ile Arg Phe Thr Asn Thr Arg
        300                 305                 310

GGA CCA GGA TTT AGC TTG ATC GCT TAT CCG GAT AAT GGT ATT CCG
                                                               — 1289
CCT GGT CCT AAA TCG AAC TAG CGA ATA GGC CTA TTA CCA TAA GGC
Gly Pro Gly Phe Ser Leu Ile Ala Tyr Pro Asp Asn Gly Ile Pro
        315                 320                 325

TCA GGT TAC ATT GTT AGA GAT ATA AGA GGA GAG TAT TTA GGG TTC
                                                               — 1334
AGT CCA ATG TAA CAA TCT CTA TAT TCT CCT CTC ATA AAT CCC AAG
Ser Gly Tyr Ile Val Arg Asp Ile Arg Gly Glu Tyr Leu Gly Phe
        330                 335                 340

GCA AAT AAT AAA AAA GCA GGT TGT GTG CTT TTT GAT TCA TCG CAA
                                                               — 1379
CGT TTA TTA TTT TTT CGT CCA ACA CAC GAA AAA CTA AGT AGC GTT
Ala Asn Asn Lys Lys Ala Gly Cys Val Leu Phe Asp Ser Ser Gln
        345                 350                 355

AAT ACG CTA ATT GAT GGT GTG ATA GCC AGA AAT TAT CCT CAG TTT
                                                               — 1424
TTA TGC GAT TAA CTA CCA CAC TAT CGG TCT TTA ATA GGA GTC AAA
Asn Thr Leu Ile Asp Gly Val Ile Ala Arg Asn Tyr Pro Gln Phe
        360                 365                 370
```

FIG. 1D

```
GGT GCA GTG GAA CTT AAA ACA GCA GCA AAA TAT AAC ATT GTC AGC
                                                                — 1469
CCA CGT CAC CTT GAA TTT TGT CGT CGT TTT ATA TTG TAA CAG TCG
Gly Ala Val Glu Leu Lys Thr Ala Ala Lys Tyr Asn Ile Val Ser
            375             380             385

ATT GTT ATT GGT GAA GAG TGT CAG CAC GTT GTT TAC AAT GGA ACT
                                                                — 1514
TAA CAA CCA CCA CTT CTC ACA GTC GTG CAA CAA ATG TTA CCT TGA
Asn Val Ile Gly Glu Glu Cys Gln His Val Val Tyr Asn Gly Thr
            390             395             400

GAG ACG GAA ACT GCC CCA ACG AAT AAT ATC ATT AGC AGT GTA ATG
                                                                — 1559
CTC TGC CTT TGA CGG GGT TGC TTA TTA TAG TAA TCG TCA CAT TAC
Glu Thr Glu Thr Ala Pro Thr Asn Asn Ile Ile Ser Ser Val Met
            405             410             415

GCT AAC AAC CCA AAA TAC GCC GCA GTA GTT GTT GGC AAG GGG ACT
                                                                — 1604
CGA TTG TTG GGT TTT ATG CGG CGT CAT CAA CAA CCG TTC CCC TGA
Ala Asn Asn Pro Lys Tyr Ala Ala Val Val Val Gly Lys Gly Thr
            420             425             430

GGT AAC CTG ATT TCG GAT GTG CTG GTT GAT TAC TCT GAA TCG GAC
                                                                — 1649
CCA TTG GAC TAA AGC CTA CAC GAC CAA CTA ATG AGA CTT AGC CTG
Gly Asn Leu Ile Ser Asp Val Leu Val Asp Tyr Ser Glu Ser Asp
            435             440             445

GCA AAG CAG GCG CAC GGC GTC ACC GTT CAG GGA AAT AAT AAT ATT
                                                                — 1694
CGT TTC GTC CGC GTG CCG CAG TGG CAA GTC CCT TTA TTA TTA TAA
Ala Lys Gln Ala His Gly Val Thr Val Gln Gly Asn Asn Asn Ile
            450             455             460

GCC AGT AAT ATT CTA ATG ACT GGG TGT GAT GGG AAA AAT GAA TCA
                                                                — 1739
CGG TCA TTA TAA GAT TAC TGA CCC ACA CTA CCC TTT TTA CTT AGT
Ala Ser Asn Ile Leu Met Thr Gly Cys Asp Gly Lys Asn Glu Ser
            465             470             475

GGA GAT CTG CAG ACA TCT ACA ACC ATT CGT TTC TTA GAT GCT GCA
                                                                — 1784
CCT CTA GAC GTC TGT AGA TGT TGG TAA GCA AAG AAT CTA CGA CGT
Gly Asp Leu Gln Thr Ser Thr Thr Ile Arg Phe Leu Asp Ala Ala
            480             485             490

CGC AGT AAT TAT GCG TCA ATA TTC CCC ATG TAT AGT TCT TCC GGC
                                                                — 1829
GCG TCA TTA ATA CGC AGT TAT AAG GGG TAC ATA TCA AGA AGG CCG
Arg Ser Asn Tyr Ala Ser Ile Phe Pro Met Tyr Ser Ser Ser Gly
            495             500             505

GTG GTT ACC TTC GAG GAA GGG TGT ATC AGG AAC TTT GTT GAA ATT
                                                                — 1874
CAC CAA TGG AAG CTC CTT CCC ACA TAG TCC TTG AAA CAA CTT TAA
Val Val Thr Phe Glu Glu Gly Cys Ile Arg Asn Phe Val Glu Ile
            510             515             520
```

FIG. 1E

```
AAA CAT CCG GGT GAC AGA AAT AAT ATT CTG AGT TCT GCA TCA GCG
─── ─── ─── ─── ─── ─── ─── ─── ─── ─── ─── ─── ─── ─── ───  ─ 1919
TTT GTA GGC CCA CTG TCT TTA TTA TAA GAC TCA AGA CGT AGT CGC
Lys His Pro Gly Asp Arg Asn Asn Ile Leu Ser Ser Ala Ser Ala
        525                 530                 535

GTG ACT GGT ATT TCC AGT ATA GAC GGC ACT ACA AAT AGC AAT GTT
─── ─── ─── ─── ─── ─── ─── ─── ─── ─── ─── ─── ─── ─── ───  ─ 1964
CAC TGA CCA TAA AGG TCA TAT CTG CCG TGA TGT TTA TCG TTA CAA
Val Thr Gly Ile Ser Ser Ile Asp Gly Thr Thr Asn Ser Asn Val
        540                 545                 550

GTT CAC GTC CCT GCG CTT GGT CAG TAC GTT GGG ACT ATG TCA GGG
─── ─── ─── ─── ─── ─── ─── ─── ─── ─── ─── ─── ─── ─── ───  ─ 2009
CAA GTG CAG GGA CGC GAA CCA GTC ATG CAA CCC TGA TAC AGT CCC
Val His Val Pro Ala Leu Gly Gln Tyr Val Gly Thr Met Ser Gly
        555                 560                 565

CGT TTT GAA TGG TGG GTT AAA TAT TTT AAC CTT GCT AAC CAG ACG
─── ─── ─── ─── ─── ─── ─── ─── ─── ─── ─── ─── ─── ─── ───  ─ 2054
GCA AAA CTT ACC ACC CAA TTT ATA AAA TTG GAA CGA TTG GTC TGC
Arg Phe Glu Trp Trp Val Lys Tyr Phe Asn Leu Ala Asn Gln Thr
        570                 575                 580

CTT GTT TCT GCA GAT AAA TTC AGA ATG CTT GCT GAA GGC GAT GTA
─── ─── ─── ─── ─── ─── ─── ─── ─── ─── ─── ─── ─── ─── ───  ─ 2099
GAA CAA AGA CGT CTA TTT AAG TCT TAC GAA CGA CTT CCG CTA CAT
Leu Val Ser Ala Asp Lys Phe Arg Met Leu Ala Glu Gly Asp Val
        585                 590                 595

TCT CTG GCT GTG GGA GGC GGT ATA AGT TCG CAA TTG AAA TTA TTC
─── ─── ─── ─── ─── ─── ─── ─── ─── ─── ─── ─── ─── ─── ───  ─ 2144
AGA GAC CGA CAC CCT CCG CCA TAT TCA AGC GTT AAC TTT AAT AAG
Ser Leu Ala Val Gly Gly Gly Ile Ser Ser Gln Leu Lys Leu Phe
        600                 605                 610

AAT AGT GAT AAT ACT AAA GGC ACT ATG TCG CTA ATA AAT GGA AAT
─── ─── ─── ─── ─── ─── ─── ─── ─── ─── ─── ─── ─── ─── ───  ─ 2189
TTA TCA CTA TTA TGA TTT CCG TGA TAC AGC GAT TAT TTA CCT TTA
Asn Ser Asp Asn Thr Lys Gly Thr Met Ser Leu Ile Asn Gly Asn
        615                 620                 625

ATT CGA ATA TCT ACT GGA AAT TCA GAA TAT ATA CAG TTT TCT GAT
─── ─── ─── ─── ─── ─── ─── ─── ─── ─── ─── ─── ─── ─── ───  ─ 2234
TAA GCT TAT AGA TGA CCT TTA AGT CTT ATA TAT CTC AAA AGA CTA
Ile Arg Ile Ser Thr Gly Asn Ser Glu Tyr Ile Gln Phe Ser Asp
        630                 635                 640

TCA GCC ATG ACA CCA TCG ACA ACG AAT ACT TAT TCT CTT GGG TTG
─── ─── ─── ─── ─── ─── ─── ─── ─── ─── ─── ─── ─── ─── ───  ─ 2279
AGT CGG TAC TGT GGT AGC TGT TGC TTA TGA ATA AGA GAA CCC AAC
Ser Ala Met Thr Pro Ser Thr Thr Asn Thr Tyr Ser Leu Gly Leu
        645                 650                 655

GCT GGT CGT GCA TGG TCG GGG GGA TTT ACC CAG TCA GCG TTT ACG
─── ─── ─── ─── ─── ─── ─── ─── ─── ─── ─── ─── ─── ─── ───  ─ 2324
CGA CCA GCA CGT ACC AGC CCC CCT AAA TGG GTC AGT CGC AAA TGC
Ala Gly Arg Ala Trp Ser Gly Gly Phe Thr Gln Ser Ala Phe Thr
        660                 665                 670
```

FIG. 1F

```
GTG CTG TCC GAT GCG CGT TTC AAG ACT GCT CCA GAG GTT ATT GAT
--- --- --- --- --- --- --- --- --- --- --- --- --- --- --- 2369
CAC GAC AGG CTA CGC GCA AAG TTC TGA CGA GGT CTC CAA TAA CTA
Val Leu Ser Asp Ala Arg Phe Lys Thr Ala Pro Glu Val Ile Asp
            675             680             685

GAG AAA ATA CTG GAC GCA TGG GAA AGA GTG GAA TGG GTT TCA TAC
--- --- --- --- --- --- --- --- --- --- --- --- --- --- --- 2414
CTC TTT TAT GAC CTG CGT ACC CTT TCT CAC CTT ACC CAA AGT ATG
Glu Lys Ile Leu Asp Ala Trp Glu Arg Val Glu Trp Val Ser Tyr
            690             695             700

CAG TAC CTT GAC AGG ATC GAA GTG AAA GGT AAA GAC GGA GCA AGA
--- --- --- --- --- --- --- --- --- --- --- --- --- --- --- 2459
GTC ATG GAA CTG TCC TAG CTT CAC TTT CCA TTT CTG CCT CGT TCT
Gln Tyr Leu Asp Arg Ile Glu Val Lys Gly Lys Asp Gly Ala Arg
            705             710             715

TGG CAC TTT GGT GCA GTT GCG CAG CAT GTT ATC AGT GTA TTT CAG
--- --- --- --- --- --- --- --- --- --- --- --- --- --- --- 2504
ACC GTG AAA CCA CGT CAA CGC GTC GTA CAA TAG TCA CAT AAA GTC
Trp His Phe Gly Ala Val Ala Gln His Val Ile Ser Val Phe Gln
            720             725             730

AAT GAA GGC ATA GAT GTG TCA CGA CTG GCA TTT ATC TGT TAT GAC
--- --- --- --- --- --- --- --- --- --- --- --- --- --- --- 2549
TTA CTT CCG TAT CTA CAC AGT GCT GAC CGT AAA TAG ACA ATA CTG
Asn Glu Gly Ile Asp Val Ser Arg Leu Ala Phe Ile Cys Tyr Asp
            735             740             745

AAG TGG AAT GAG ACC CCG GCA GAA TAC AGG GAT GTG ACG GAA GAA
--- --- --- --- --- --- --- --- --- --- --- --- --- --- --- 2594
TTC ACC TTA CTC TGG GGC CGT CTT ATG TCC CTA CAC TGC CTT CTT
Lys Trp Asn Glu Thr Pro Ala Glu Tyr Arg Asp Val Thr Glu Glu
            750             755             760

GAG CAT TCT GCA GGA GTT TAC CCA CTT ATA CAG ACA AAG GTT CTG
--- --- --- --- --- --- --- --- --- --- --- --- --- --- --- 2639
CTC GTA AGA CGT CCT CAA ATG GGT GAA TAT GTC TGT TTC CAA GAC
Glu His Ser Ala Gly Val Tyr Pro Leu Ile Gln Thr Lys Val Leu
            765             770             775

GTA CGC GAA GCC GTC GAG GCT GGT GAA TGT TAC GGT ATC CGT TAT
--- --- --- --- --- --- --- --- --- --- --- --- --- --- --- 2684
CAT GCG CTT CGG CAG CTC CGA CCA CTT ACA ATG CAA TAG GCA ATA
Val Arg Glu Ala Val Glu Ala Gly Glu Cys Tyr Gly Ile Arg Tyr
            780             785             790

GAA GAG GCT CTG ATT CTG GAA TCT GCG ATG ATG AGA CGC AGG GTT
--- --- --- --- --- --- --- --- --- --- --- --- --- --- --- 2729
CTT CTC CGA GAC TAA GAC CTT AGA CGC TAC TAC TCT GCG TCC CAA
Glu Glu Ala Leu Ile Leu Glu Ser Ala Met Met Arg Arg Arg Val
            795             800             805

AAA AAG CTG GAA GAG CAA GTT TTG CAA TTA ACA GGG AAT
--- --- --- --- --- --- --- --- --- --- --- --- ---         2768
TTT TTC GAC CTT CTC GTT CAA AAC GTT AAT TGT CCC TTA
Lys Lys Leu Glu Glu Gln Val Leu Gln Leu Thr Gly Asn
            810             815             820
```

FIG. 1G

```
TGAACCGTAA  ATGGTGTGTT  GTTGCGCGGT  ATACTTTTCC  TGAAGCAGGG
──────────  ──────────  ──────────  ──────────  ──────────  2818
ACTTGGCATT  TACCACACAA  CAACGCGCCA  TATGAAAAGG  ACTTCGTCCC

TGTTTGCAAA  TAAACGGGTT  TCGTTATGTC  ATTCCAACTA  ACCAATGAAA
──────────  ──────────  ──────────  ──────────  ──────────  2868
ACAAACGTTT  ATTTGCCCAA  AGCAATACAG  TAAGGTTGAT  TGGTTACTTT

CTTCAAATCA  GTGGCTTAGT  GTTAGTTCTC  TTGCTGCGGT  TATTGCAGGT
──────────  ──────────  ──────────  ──────────  ──────────  2918
GAAGTTTAGT  CACCGAATCA  CAATCAAGAG  AACGACGCCA  ATAACGTCCA

GTCCCTCCGG  AGGTTGCTTT  GGGGGCTTTG  GCTGGGGCGG  TAATTTTTGT
──────────  ──────────  ──────────  ──────────  ──────────  2968
CAGGGAGGCC  TCCAACGAAA  CCCCCGAAAC  CGACCCCGCC  ATTAAAAACA

TACCTCTGCG  GTAGAGTATC  CTATTCGTCG  TCGTGTACTC  TTGTCGATGC
──────────  ──────────  ──────────  ──────────  ──────────  3018
ATGGAGACGC  CATCTCATAG  GATAAGCAGC  AGCACATGAG  AACAGCTACG

TTAGCTTTCT  CTGCGGCCTT  CTTTTTTATA  AACCAGCAGC  ATCAATTCTT
──────────  ──────────  ──────────  ──────────  ──────────  3068
AATCGAAAGA  GACGCCGGAA  GAAAAAATAT  TTGGTCGTCG  TAGTTAAGAA

ATCGGCATAG  CCAGCCTGAT  C
──────────  ──────────  ─  3089
TAGCCGTATC  GGTCGGACTA  G
```

DNA FRAGMENT CARRYING THE GENE ENCODING THE ENZYME FOR FRAGMENTING N-ACETYLHEPAROSAN AND THE ADJACENT SEQUENCES PERMITTING ITS EXPRESSION, RECOMBINANT ENZYME INTENDED FOR FRAGMENTING N-ACETYLHEPAROSAN AND ITS USE

The present invention relates to a DNA fragment carrying the gene encoding the enzyme for fragmenting high molecular mass across N-acetylheparosan and to the adjacent sequences permitting the expression of this gene, a recombinant enzyme intended for fragmenting N-acetylheparosan containing this gene, the production of preparations containing this recombinant enzyme as well as processes for fragmenting N-acetylheparosan using this enzyme.

It is known that some bacteria of the *Escherichia coli* species produce a capsular polysaccharide, normally called K5, which is a family of polymers consisting of repetitive β-D-glucuronyl-1,4-α-N-acetyl-D-glucosaminyl units (1,4) (W. F. Vann et al., Eur. J. Biochem, 1981, 116, 359–364), of structure (a):

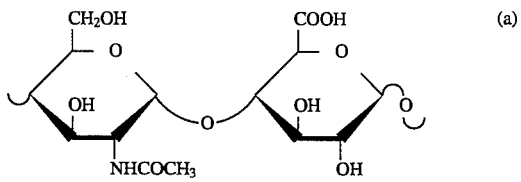

This polysaccharide will be called here "N-acetylheparosan". This product has at the level of the "uronic acid" units, a regular structure composed only of D-glucuronic acid. Its molecular mass is between $10^5$ and $2.10^6$ Da. It is therefore an N-acetylheparosan of high molecular mass.

N-acetylheparosan is useful as raw material for the pharmaceutical industry but, for this use, it has a too high molecular mass. As example, reference can be made to Patent Applications EP-0,333,243 and EP-0,489,647 which relate to low molecular mass N-acetylheparosan derivatives or to products obtained from low molecular mass N-acetylheparosan. The various products described in these two applications possess highly valuable pharmacological properties. Their molecular masses are less than or equal to 15,000 Da.

It is known that N-acetylheparosan (K5 polysaccharide) can be fragmented by a phage lyase derived from a phage specific for the *Escherichia coli* strain (K5), but this fragmentation is very extensive and leads to a substantial disappearance of the fragments with a molecular mass of 5,000 Da into much smaller chains, with molecular masses of less than 1,000 Da (D. Gupta et al., FEMS Microbiology Letters, (1983), 16, 13–17). This type of fragmentation is used in Patent Application EP-A-0,333,243 for the preparation of fragments containing a maximum of 10 saccharide units.

It has also been observed that cultures of *Escherichia coli* (K5), strain SEBR 3282, produce under certain environmental conditions, an enzyme which fragments N-acetylheparosan during culture in a fermenter. The strain SEBR 3282 of *Escherichia coli* (K5) responds positively to the typing test with the K5-specific phage, according to the method of B. Kaiser et al. (J. Clin. Microbiol., (1984), 19, 2, 264–266). It is therefore indeed an *Escherichia coli* (K5) strain. This strain was deposited at the Collection Nationale de Cultures de Microorganisms (CNCM) of the Institut Pasteur, Paris, France, under N° 1-1013.

The enzyme obtained from the strain SEBR 3282 of *Escherichia coli* (K5) has a molecular mass of between 62,000 and 70,000 Da (measured by exclusion HPLC), its isoelectric point is situated in the pH region of between 4.7 and 5.4 pH units and it is an eliminase.

This enzyme is also characterized in that it acts in the following manner:

- it is of membrane origin,
- the temperature for its optimum operation (maximum activity) is close to 37° C. and the temperature at which it is inactivated is about 60° C.,
- the optimum zone of pH for its operation is situated between the pH 6 and pH 7 values,
- for its operation, the optimum zone of concentration of monovalent or divalent ions is situated in the vicinity of 0.2 M.

The enzyme obtained from the abovementioned strain is capable of acting on high molecular mass N-acetylheparosan and of fragmenting it in the absence of bacterial body in vitro and makes it posible to obtain, under certain conditions, N-acetylheparosan fragments situated around a peak with a molecular mass of about 5,000 Da, corresponding to within a few disaccharide units, about 70% of the product.

It was observed, moreover, that a preparation of this enzyme suitably solubilized, makes it possible to obtain fragments of higher molecular mass compared with the fragments obtained spontaneously, that is to say with the non-solubilized enzyme. Indeed, preparations of solubilized enzyme make it possible to modulate the fragmentation and to obtain fragments of which the majority has a molecular mass greater by at least 1,000 to 3,000 Da compared with the molecular mass of the fragments obtained spontaneously.

However, the industrial use of this enzyme and in particular in a soluble form and preparations containing it is limited by the small quantities available from the strain SEBR 3282 of *Escherichia coli* (K5).

Moreover, the production of preparations of the solubilized enzyme requires a number of operations such as the solubilization of the enzyme by means of detergents or strong inorganic bases. These manipulations also increase the cost of preparing the various low molecular mass N-acetylheparosans used as raw material in the pharmaceutical industry.

To overcome these disadvantages, research studies in this domain have been carried out and have permitted the isolation of a DNA fragment carrying the gene encoding an enzyme for fragmenting high molecular mass N-acetylheparosan. The introduction, into an expression vector, of the DNA fragment carrying the sequence encoding the enzyme has made it possible to obtain large quantities of a recombinant enzyme intended for fragmenting high molecular mass N-acetylheparosan.

Surprisingly, it was observed that starting with this same DNA fragment it is possible to obtain the recombinant enzyme in two different forms: the first form of the enzyme is associated with the cellular pellet (that is to say about 90% of the enzymatic activity) and is termed membrane form like the enzyme obtained from the wild-type strain; the second form of the enzyme is present spontaneously in the supernatant, in a substantial quantity and is termed soluble form.

Indeed, it was observed that a nucleotide sequence of the cloned DNA fragment makes it possible to obtain constructs spontaneously expressing a high percentage of the enzyme being in a soluble form, that is to say directly in the culture supernatant. The soluble form of the enzyme prepared from the culture supernatant and used under defined conditions makes it possible to fragment the high molecular mass N-acetylheparosan completely and precisely into fragments assembled around a predominant peak corresponding to 9–10 disaccharide units, which corresponds to a molecular mass of about 5,000 Da, evaluated by exclusion HPLC. The dispersion of the fragments around this predominant peak is very low. A disaccharide unit of N-acetylheparosan corresponds to the disaccharide unit represented by the formula (a).

This possibility, of obtaining N-acetylheparosan fragments weakly dispersed at the level of their molecular mass, offered by the recombinant enzyme in a soluble form, dispenses from any subsequent fractionation whatsoever, especially by exclusion chromatography.

Furthermore, by modifying the operating conditions, it is possible, still by resorting to the soluble form of the enzyme, to obtain N-acetylheparosan fragments of size less than or greater than the 9–10 repetitive disaccharide units mentioned above. To obtain fragments whose size is less than the 9–10 repetitive units, it is also possible to use, in particular, the membrane forms of the enzyme.

Moreover, irrespective of the form, soluble or membrane, of the enzyme, the enzymatic reaction can be carried out incompletely in order to obtain a mixture of fragments of sizes greater than the 9–10 disaccharide units mentioned above.

The present invention therefore relates to a DNA fragment carrying a gene encoding the enzyme intended for fragmenting a high molecular mass N-acetylheparosan, the recombinant enzyme encoded by this gene, the various forms of the recombinant enzyme derived from this sequence, especially the membrane form and the soluble form of this enzyme, as well as fragmentation processes using this recombinant enzyme.

The DNA fragment carrying the gene encoding the enzyme intended for fragmenting N-acetylheparosan and the expression systems permitting its biosynthesis, corresponds to the sequence SEQ ID N° 1.

FIG. 1 depict a double-stranded nucleotide sequence, which is supplemented with a reading frame of 820 amino acids.

This DNA fragment, whose exact size is 3089 base pairs (bp) carries the gene encoding the enzyme for fragmenting high molecular mass N-acetylheparosan, but also the regulatory signals permitting its expression. These regulatory signals are mainly:

1-a specific promoter, which is essential for the transcription of the gene
2-a ribosome-binding site which is essential for carrying out the translation of the protein from the transcribed mRNA.

Computer analysis reveals several reading frames. Reading frame is understood to mean an amino acid sequence deduced from the nucleotide sequence via the genetic code which starts with a methionine coded by ATG and which ends with one of the stop codons TAA, TGA or TAG.

Several possible reading frames whose size is less than 100 amino acids exist in this DNA fragment. There is also a reading frame of 820 amino acids characterized in that it has the peptide sequence SEQ ID N° 2.

The sequence SEQ ID N° 2 is also the subject of the present invention.

The invention also relates to any DNA fragment comprising the reading frame or part thereof which gives the peptide sequence or derived from the peptide sequence.

The invention also relates to a strain carrying a plasmid permitting the production of a recombinant enzyme which fragments high molecular mass N-acetylheparosan. Such a strain has been deposited under the Budapest Treaty at the CNCM of the Institut Pasteur, Paris, France on 6 Aug. 1993, under the number 1-1352.

The strain carrying a plasmid permitting the production of a recombinant enzyme which fragments high molecular mass N-acetylheparosan is a recombinant strain from the strain RRI of *Escherichia coli* (K12) provided by GIBCO-BRL (ref. 530–8231 SA). Other appropriate *Escherichia coli* strains can be envisaged.

As vector, there has been used the vector pUC 18 hydrolysed by BamHI/BAP (Pharmacia® ref. 27-4855-01), into which the DNA fragment corresponding to the sequence SEQ ID N° 1 has been introduced.

However, to obtain a strain carrying a plasmid permitting production of a recombinant enzyme which fragments high molecular mass N-acetylheparosan, it is possible to envisage the use of other vectors and/or as indicated above, of other recipient strains.

As other vectors, it is possible to use vectors such as pBR 322 (Pharmacia® ref. 274902-01) or any other vector into which it is possible to insert all the DNA-fragment corresponding to the sequence SEQ ID N° 1 or part of-this DNA fragment carrying the sequence necessary for the expression of the protein of 820 amino acids, this translated sequence being the sequence SEQ ID N° 2.

Apart from the recipient strain RRI of *Escherichia coli* (K12), other Gram-negative strains can be used provided however that the regulatory system for the protein containing 820 amino acids and having the peptide sequence SEQ ID N° 2 is compatible with the host cell.

The strain deposited at the CNCM of the Pasteur Institute, Paris, France, on 6 Aug. 1993 under the number 1-1352 is a strain obtained by transforming the strain RRI of *Escherichia coli* (K12) with a vector carrying a DNA fragment corresponding to the sequence SEQ ID N° 1 and therefore, carrying the sequence necessary for the expression of the protein of 820 amino acids which is the sequence SEQ ID N° 2 (translated sequence).

However, it is possible to envisage a number of strains which produce a recombinant enzyme intended for fragmenting high molecular mass N-acetylheparosan which is obtained by transforming the strain RRI of *Escherichia coli* (K12), or other suitable Gram-negative strains, with vectors carrying DNA fragments derived from the SEQ ID NO: 1 sequence and carrying at most the sequences necessary for the expression of the protein of 820 amino acids. These translated sequences are:

either the sequence SEQ ID N° 2 as a whole, corresponding to amino acids 1 to 820, or the entire amino acids 112 to 820 of the sequence SEQ ID N° 2, or the entire amino acids 160 to 820 of the sequence SEQ ID N° 2, or the entire amino acids 194 to 820 of the sequence SEQ ID N° 2.

The invention therefore relates in particular to a DNA fragment encoding all or part of the sequence SEQ ID N° 2 as indicated above.

The invention relates, in particular, to a gene encoding an enzyme intended for fragmenting N-acetylheparosan which is carried by the DNA fragment of the nucleotide sequence.

The invention relates more particularly to a recombinant enzyme intended for fragmenting high molecular mass N-acetylheparosan which is derived from the gene mentioned above. This gene comprises a DNA sequence encoding all or part of the peptide sequence SEQ ID N° 2.

Expression vectors characterized in that they carry, with the means necessary for the expression, the DNA fragment encoding the protein SEQ ID N° 2 capable of fragmenting N-acetylheparosan also form part of the invention.

To obtain the recombinant enzyme which is the subject of the present invention, the vector p466, which is described in detail in Patent Application EP-0,480,461, was used as vector.

However, it is also possible to use other expression vectors, for example those described by Studier FW and Moffatt BA in J. Mol. Biol (1986), 189, pp. 113–130 and to transform one of the recipient strains recommended by these authors.

The subject of the invention is also more particularly the plasmid p868,26. This plasmid was obtained by ligating a fragment of the plasmid p466 to a DNA fragment obtained after the polymerase chain reaction using an oligonucleotide whose sequence is the following:

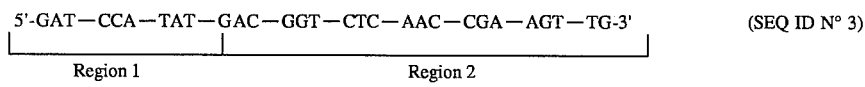 (SEQ ID N° 3)

in the presence of an oligonucleotide whose sequence is the following:

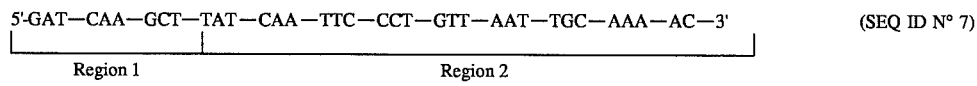 (SEQ ID N° 7)

A=deoxyadenosine-5'-phosphoric acid
C=deoxyguanosine-5'-phosphoric acid
G=deoxycytidine-5'-phosphoric acid
T=deoxythymidine-5'-phosphoric acid.

The subject of the invention is also a bacterial strain, the bacterial strain TP 2339 transformed with the plasmid p868, 26. This strain makes it possible to obtain the recombinant enzyme which is the subject of the present invention both in soluble form and in membrane form.

In the wild-type *Escherichia coli* strain, the induction of the enzyme is dependent in a complex manner on the components of the culture medium. In contrast, the method of obtaining the recombinant enzyme, which is the subject of the present invention, makes it possible to dispense with the complex natural raw materials, in particular of animal origin. Indeed, the gene encoding the recombinant enzyme is placed under the control of an inducible promoter made functional simply by adding IPTG (isopropyl-β-D-thiogalactoside) at the time judged most appropriate for the desired aim. For example, the time chosen for the induction will be situated in the exponential phase of the culture, at half the predictable maximum biomass.

The techniques used for introducing a DNA fragment encoding an enzyme for fragmenting high molecular mass N-acetylheparosan into an expression vector permitting large quantities of this enzyme to be obtained, are techniques which are well known to persons skilled in the art. They are presented in detail in the book by Sambrook Fritsch and Maniatis "Molecular cloning: A Laboratory manual" published in 1989 by the publishers Cold Spring Harbor Press (N.Y.) 2nd edition.

The recombinant enzyme which is the subject of the present invention makes it possible to fragment N-acetylheparosan and to obtain fragments comprising, at the non-reducing end, a glucuronic acid residue having a double bond between carbons 4 and 5 (removal of the OH group). Such enzymes do not require water in the chemical reaction considered and are said to be of the eliminase type. The recombinant enzyme which is the subject of the present invention is therefore an eliminase and especially an endo-β-eliminase.

The recombinant enzyme which is the subject of the present invention can be used for fragmenting high molecular mass N-acetylheparosan either in its membrane form or in its soluble form.

The membrane form of the recombinant enzyme is present spontaneously in the bacterial pellet after centrifugation or filtration of the culture of the recombinant strain. An extraction of the pellet in the presence of Triton X-100 makes it possible to obtain the recombinant enzyme in soluble form. This extraction is made for example using an extraction buffer consisting of:

Tris.HCl 25 mM
NaCl 9 g/l
Triton X-100 30 g/l
(pH=7.0)

The bacterial pellet of the *Escherichia coli* strain recombinant enzyme is resuspended in the extraction buffer. After allowing to stand for 1 hour at room temperature, the culture suspension is centrifuged and the supernatant stored. The supernatant can be used as it is since the triton X-100 has no inhibitory effect on the enzyme.

The soluble form of the enzyme is also present spontaneously in the recombinant strain culture supernatant. It is therefore possible to isolate it from the supernatant by removing the bacteria from the culture by centrifugation or by microfiltration.

The soluble recombinant enzyme can be stored at the temperature of −20° C.

The term "preparation containing the enzyme" includes both the preparations containing the membrane form of the enzyme and the preparations containing the soluble form of the enzyme.

The preparations containing the recombinant enzyme in soluble form or in membrane form also form part of the invention. The various preparations containing the recombinant enzyme which is the subject of the present invention and especially the preparations containing the enzyme in membrane form or in soluble form are particularly useful for preparing low molecular mass N-acetylheparosans, for the following reasons:

the high molecular mass N-acetylheparosan is obtained in inexpensive synthetic medium with yields higher than those of a complex medium, a medium necessary for producing a small molecular mass N-acetylheparosan;

the high molecular mass N-acetylheparosan is technically easier to handle than that of small molecular mass;

the in vitro fragmentation separates the production phase from that of fragmentation, which makes it possible to control and optimize both phases while offering a wide scope in relation to the characteristics of the desired product, for example in relation to its molecular mass;

the recombinant enzyme and the high molecular mass N-acetylheparosan are particularly stable, which allows multiple recyclings which may be necessary in the implementation of dynamic processes, during which the fragmentation and fractionation processes are implemented simultaneously or successively while dispensing with the time constraints linked to the use of a bioreactor;

a recombinant strain, unlike the wild-type strain SEBR 3282 *Escherichia coli* (K5), makes it possible to fragment large quantities of high molecular mass N-acetylheparosan. Indeed, 1 liter of culture supernatant containing the recombinant enzyme is capable of fragmenting about 10–100 liters of N-acetylheparosan culture, which corresponds to 30–400 g of high molecular mass N-acetylheparosan.

To obtain a small molecular mass N-acetylheparosan having fragments corresponding to 9–10 disaccharide units, the soluble recombinant enzyme obtained spontaneously in the culture supernatant of the recombinant strain which is the subject of the present invention is preferably used. The final concentration of the high molecular mass N-acetylheparosan subjected to the action of the soluble enzyme is 2–30 g/l, more particularly 8–12 g/l, preferably 10 g/l.

The soluble enzyme is diluted such that a quantity of high molecular mass N-acetylheparosan 10–100%, preferably 50%, higher than that effectively used, which is 10 g/l, can be fragmented during a reaction lasting 2 hours to 48 hours, preferably 16 to 24 hours.

The enzymatic reaction is carried out preferably in the presence of sodium chloride at pH 7 and at 37° C., with gentle stirring. The reaction is sufficiently slow to permit monitoring of the fragmentation of the high molecular mass N-acetylheparosan. This monitoring is performed by evaluating the molecular mass of the fragmented N-acetylheparosan by exclusion HPLC.

To obtain N-acetylheparosan fragments of size less than 9–10 disaccharide units, several alternatives are possible and especially:

either the soluble enzyme is used in the presence of calcium ions in substantial concentration, or the recombinant enzyme is used in membrane form, or the duration of the enzymatic fragmentation reaction is increased, or the concentration of the dilute enzyme used for fragmenting the high molecular mass N-acetylheparosan is increased.

As calcium salt, calcium chloride can be used. The concentration of calcium ions is of the order of 1–300 mM, preferably 100 mM.

With the aim of obtaining N-acetylheparosan fragments of size greater than 9–10 disaccharide units, a partial enzymatic reaction is simply carried out, for example by limiting its duration. In this case, the various forms of the recombinant enzyme (membrane or soluble) can be equally used.

To stop the enzymatic reaction, several means can be used and especially:

cold temperature up to 4° C., the activity of the recombinant enzyme is reduced, heat since the N-acetylheparosan is resistant to a temperature of about 60° C. and that the enzyme is inactivated at this temperature, basic pH: the recombinant enzyme and N-acetylheparosan are resistant to pH 11 but the activity of the enzyme in this pH zone is reduced or zero, acidic pH, for example pH 4 or, 80% ethanol which inactivates the enzyme and precipitates N-acetylheparosan.

The invention also relates to processes for fragmenting a high molecular mass N-acetylheparosan using the recombinant enzyme which is the subject of the present invention.

For the implementation of the invention, the preparation of N-acetylheparosan predominantly of high molecular mass proved to be necessary. It does not form part of the invention but this preparation is also presented in detail below.

The production of the DNA fragment carrying the gene encoding the enzyme for fragmenting N-acetylheparosan and the adjacent sequences permitting its expression, its characterization as well as the various genetic engineering tools and processes which have permitted the production of the recombinant enzyme, are described in detail below in the different "sections".

An example of the use of the enzyme for fragmenting high molecular mass N-acetylheparosan illustrates the use of the recombinant enzyme which is the subject of the present invention.

It is given with no limitation being implied.

PREPARATION

N-ACETYLHEPAROSAN OF PREDOMINANTLY HIGH MOLECULAR MASS 400 ml of the medium B, of a composition which is specified in Table I below, are inoculated with the strain SEBR 3282 of *Escherichia coli* (K5) deposited at the CNCM of the Pasteur Institute, Paris - France, under No. I-1013, and the mixture is incubated, with stirring, for 2 hours at 37° C. The preculture obtained is then transferred into an 18.5 liter fermenter containing 11 liters of the medium A, of a composition which is also specified in Table I below, and the mixture is incubated for 6 hours and 30 minutes at 37° C. and a pH equal to 7.2, the partial pressure of oxygen being maintained at 40 mmHg by regulating the injection of air (up to 20 l/minute) and the stirring. Glycerol is then added by continuously introducing a sterile solution containing 500 g/l of glycerol at the rate of 18 g/h for 16–17 hours.

The culture is continued under the same conditions of temperature, pH and partial pressure of oxygen until practically all the glycerol has been consumed. The monitoring of the optical density (OD) at $\lambda$=600 nm of the culture suspension at the end of the addition of glycerol, shows a stationary or slight lysis state until the culture is stopped at 28–30 hours old in the fermenter.

The culture suspension is then cooled to 25° C., centrifuged from 11,000 to 14,000 g for 15 to 20 minutes. The supernatant is supplemented with 0.1M NaOH (the pH increases to about 10) and again centrifuged. The resulting supernatant is then concentrated without delay in Amicon® hollow fiber cartridges with a 10 kD cut-off or equivalent, and then the solution is neutralized (pH=7). A solution enriched with high molecular mass N-acetylheparosan is thus obtained. An adequate quantity of sodium chloride is added to the solution in order to have a final NaCl concentration of 0.5 M, and then 4 volumes of ethanol are added. The precipitate is allowed to form overnight at 4° C. After a first removal of the supernatant by pumping, the precipitate is centrifuged at 5,000 g for 20 minutes at room temperature. The centrifugation pellets are taken up in ethanol, the suspension obtained is stirred and it is allowed to stand for 1 hour at room temperature. The centrifugation and suspending operations are repeated. A centrifugation is again carried out at 5,000 g for 20 minutes. The centrifugation pellets obtained are dried in a vacuum oven at 40° C. for 24 hours. The N-acetylheparosan thus obtained is a "purified high molecular mass N-acetylheparosan".

TABLE I

Composition and preparation of the medium A and the medium B.

MEDIUM A

In 900 ml of ultra-purified water dissolved in order:

| | |
|---|---|
| Tricine ®N'[Tris-(hydroxymethyl)methyl]glycine)* | 360 mg |
| $K_2HPO_4$ | 790 mg |
| Glutamic acid | 11000 mg |
| $MgCl_2.6H_2O$ | 500 mg |
| $K_2SO_4$ | 450 mg |
| $FeSO_4.7H_2O$ | 18 mg |
| $CaCl_2.2H_2O$ | 2 mg |
| NaCl | 500 mg |
| KCl | 5000 mg |
| Solution of trace elements (cf. Table II) | 1 ml |
| Glycerol | 10000 mg |

Adjust the pH to 7.2 with concentrated potassium hydroxide of density 1.38 and fill to 1000 ml with ultra-purified water. Perform a degerminating filtration on a 0.2 μm membrane.

Glycerol solution

Dissolve 50 g of glycerol in a sufficient quantity of ultra-purified water and adjust the volume to 1000 ml with the same solvent. Perform a degerminating filtration on a 0.2 μm membrane.
The antifoam used during the fermentation is Struktol J 673 ® (Schill and Seilacher).

MEDIUM B

The preparation of the medium B is identical to that of the medium A, the only difference being that it is advisable to add, in addition, the buffer (pH 7.2): 3-morpholinopropane-sulphonic acid (M.O.P.S.) after adding the antifoaming agent.

*(marketed by Fluka)

TABLE II

Preparation of the solution of trace elements in 800 ml of ultra-purified water dissolve (in order):

| | |
|---|---|
| $H_3BO_3$ | 500 mg |
| $Na_2MoO_4.2H_2O$ | 1930 mg |
| $CoCl_2.6H_2O$ | 11850 mg |
| $CuSO_4.5H_2O$ | 25 mg |
| $ZnSO_4.7H_2O$ | 2000 mg |
| $AlCl_3.6H_2O$ | 2410 mg |

Add 100 ml of hydrochloric acid of density 1.9 and fill to 1000 ml with ultra-purified water.

SECTIONS

1-PREPARATION OF THE GENOMIC DNA OF THE STRAIN SEBR 3282 OF *ESCHERICHIA COLI*

A colony of the strain SEBR 3282 of *Escherichia coli* (K5) is cultured at 37° C. with stirring, in 5 ml of LB medium (Bactotryptone 5 g/l, yeast extract 10 g/l, NaCl 5 g/l: pH 7.35) overnight. One millimeter of this culture is used to inoculate a 1 liter flask containing 100 ml of the same culture medium and incubated at 37° C. on an orbital shaker set at 180 revolutions per minute. When the optical density of the culture, measured at X=600 nm, is equal to 1, the bacteria are centrifuged for a few minutes at 10000 rpm (Beckman J2.21) and taken up in 20 ml of a buffer of the following composition: 10 mM Tris-HCl pH 8.0, 20 mM EDTA, 0.1% SDS, 50 μg/ml proteinase K (Sigma® P 2308).

This bacterial suspension is incubated for 1 hour at 60° C. The enzymatic reaction is stopped by two phenol extractions (Appligène® ref. 130181) followed by extraction with dichloromethane. The nucleic acids are precipitated in the presence of 0.1M NaCl and two volumes of ethanol, and resolubilized in 10 ml of a TE buffer (10 mM Tris HCl, pH 8.0; 1 mM EDTA) containing 10 μg/ml of RNase (Boehringer Mannheim® 1119915).

After incubating for one hour at 37° C., the solution is again subjected to two phenol extractions followed by extraction with dichloromethane. The DNA obtained is precipitated in the presence of 0.1M of NaCl and two volumes of ethanol are then resolubilized with 10 ml of TE buffer. An aliquote fraction of this DNA, about 10 μg, is subjected to partial hydrolysis with the restriction enzyme SAU3A (Appligène®) under the conditions recommended by the supplier.

The partially hydrolysed DNA is subjected to electrophoresis on 1% agarose gel in the presence of the 1Kbp (kilo base pairs) size reference (BRL ref. 520–5615 SA). The DNA band which corresponds to a size of about 3 Kbp is purified by the geneclean technique (Bio 101® ref. 3105).

An aliquot fraction (approximately 200 ng) of the genomic DNA band, hydrolysed with SAU3A and whose size is about 3 Kbp, is ligated according to the technique described in "Molecular cloning: A Laboratory manual" (Sambrook, Fritsch and Maniatis, Cold Spring Harbor Press (N.Y.) 2nd edition (1989) pp. 1:63–1:67) in the presence of the vector pUC 18 hydrolysed with BamH1 and dephosphorylated (Pharmacia® Ref. 27-4855-01) in the appropriate reaction mixture described "Molecular cloning: A Laboratory manual" (document referenced above) overnight at 4° C.

This ligation mixture is used to transform, under the conditions recommended by the supplier, the strain RRI of *Escherichia coli* (K12) (GIBCO-BRL ref. 530–8261 SA). The result is a mixture called "transformation mixture" which is plated after dilution on 10 Petri dishes containing the LB medium previously described and supplemented with 15 g/l of noble agar and 100 mg/ml of ampicillin.

After incubating overnight at 37° C., the Petri dishes become covered with about 700 colonies each derived from a clone. Each Petri dish corresponds to one pool and the ten pools are classified from A to J and grouped under the number 838. Each clone has a DNA fragment of between 3 and 4 Kbp in size. The set of ten pools represents approximately 4 times the entire genome of *Escherichia coli*.

2-PURIFICATION OF THE CLONE 838,7 PRODUCING THE ENZYME INTENDED FOR FRAGMENTING N-ACETYLHEPAROSAN

The clone having an eliminase activity was detected by the fragmentation of high molecular mass N-acetylheparosan in vitro. The fragmentation of high molecular mass N-acetylheparosan was followed by analysis of the molecular mass of the fragmented N-acetylheparosan by exclusion HPLC.

2.1-Incubation of the pools of transformed bacteria

The preceding 10 pools formed by the transformation mixture described in Section 1, are plated in Petri dishes on agar LB medium (with agar) supplemented with 100 µg/ml of ampicillin and incubated for 48 hours at 37° C. The resulting bacterial lawn is resuspended in 3 ml of buffer A (of the following composition: 100 mM bis-Tris-propane; 150 mM NaCl, the pH is adjusted to 6.6 with hydrochloric acid). These bacterial suspensions are used to carry out the enzymatic fragmentation reaction.

2.2-Enzymatic fragmentation reaction

50 µl of a solution of high molecular mass N-acetylheparosan at 20 g/l are added to 500 µl of buffer A described above. To obtain this solution, a sufficient quantity of purified high molecular mass N-acetylheparosan (Preparation) is dissolved in ultra-purified water. The reaction mixture thus constituted is incubated from 3 to 4 days in an Eppendorf tube at 40° C.

2.3-Analysis of the fragmentation products

Preparation of the samples

The reaction mixture in an Eppendorf tube is then centrifuged at 10,000 g for 3 minutes. 100 µl of the supernatant are precipitated by adding 4 volumes of ethanol and then again centrifuged under the same conditions. The resulting pellet is taken up in 300 µl of 25 mM piperazine buffer, pH 3.5 (0.215 g of anhydrous piperazine are dissolved in 90 ml of ultra-purified water; the pH is adjusted to 3.5 with 1M HCl and then the volume is adjusted to 100 ml with ultra-purified water) and loaded onto a microcolumn prefilled with 100 µl of Q-Sepharose® resin. The washing of the microcolumn is performed with 2 ml of 25 mM piperazine buffer (pH 3.5) followed by 2 ml of ultra-purified water. The elution is performed with 200 µl of NaCl 0.5M. The eluate thus prepared is used directly for analysis by exclusion HPLC chromatography.

Operating conditions for exclusion HPLC

A 65 µl sample of this eluate containing the purified N-acetylheparosan is analysed by exclusion chromatography on an isocratic HPLC chain. The operating conditions are the following:

- Column: TSK 2000 SW® (Toso-Haas) of 300×7.5 mm consisting of silica beads 1 µm in diameter and with a porosity of 125 Å.
- Eluent: 0.5 M aqueous sodium sulphate solution, filtered on a 0.2 µm filter and degassed
- Flow rate: 1 ml/min.
- UV Detection: 205 nm
- The calibration is performed by means of a range of oligosaccharides derived from heparin (10 mg) of the following molecular masses (Da): 3410, 4000, 4540, 5000, 6150, 7540, 10090.

Interpretation of the results

On the graphs obtained, the plot between the vertex of the peak corresponding to the high molecular mass species and the peak corresponding to the exit of sodium chloride is examined. If this line bends upwards compared with the control,—which reflects the presence of smaller sized N-acetylheparosan fragments—, this is considered as sign of a fragmentation activity and therefore of the presence of the desired enzyme in the pool which is the source of the reaction mixture.

2.4-Results

The pool I, among the 10 pools marked from A to J, was found to be positive and was used subsequently. An aliquote sample stored in glycerol at −80° C. was replated on a dish, and 1200 clones were obtained. These clones were analysed in tens and finally a producing clone called plasmid p838,7 was selected.

3-ANALYSIS OF THE PLASMID p838,7

The strain RRI of *Escherichia coli* (K12) transformed with the plasmid p838,7 is cultured in 500 ml of LB medium supplemented with 100 µg/ml of ampicillin. This strain has been deposited at the CNCM of the Pasteur Institute, Paris, France on 6th Aug. 1993, under the number I-1352.

The plasmid present in this strain is purified by the method of Qiagen® (Diagen® ref. 10.043). The plasmid called p838,7 is hydrolysed according to methods known to persons skilled in the art with several restriction enzymes: EcoRI, HindIII, PstI, SphI, XbaI, ScaI (New England Biolabs Beverly Mass. 01915–5599 USA). Analysis of the restriction map obtained shows that the size of the DNA fragment obtained from the genomic DNA of the strain SEBR 3282 of *Escherichia coli* (K5) is about 3100 bp. The complete determination of the sequence is then carried out by the Sanger technique described in PNAS (1977), 74, pp. 5463–5467.

The complete nucleotide sequence of the DNA fragment carrying the gene encoding the enzyme for fragmenting high molecular mass N-acetylheparosan and the expression systems permitting its biosynthesis is the SEQ ID NO: 1 sequence.

4-ANALYSIS OF THE NUCLEOTIDE SEQUENCE OF THE DNA FRAGMENT CARRYING THE ENZYMATIC ACTIVITY

The DNA fragment of $S_1$ sequence, whose exact size is 3089 bp, carries the gene encoding the enzyme for fragmenting high molecular mass N-acetylheparosan but also the regulatory signals permitting its expression. Indeed, this fragment alone is capable of ensuring the production of the enzyme for fragmenting the high molecular mass N-acetylheparosan polysaccharide. These regulatory signals are in particular:

a -a specific promoter which is essential for the transcription of the gene.

b -a ribosome-binding site which is essential for carrying out the translation of the protein from the mRNA transcribed.

Computer analysis of the nucleotide sequence reveals several reading frames. A reading frame is an amino acid sequence deduced from the nucleotide sequence, via the genetic code, which starts with a methionine encoded by ATG, and which ends with one of the stop codons TAA, TGA or TAG (Sambrook, Fritsch and Maniatis, Cold Spring Harbor Press (N.Y.) 2nd edition (1989) pp. D1). Several possible reading frames exist in the SEQ ID NO: 1 sequence whose size is less than 100 amino acids. The latter will not be described.

There is also a reading frame whose size is 820 amino acids. FIG. 1 shows the double-stranded nucleotide sequence of the SEQ ID NO: 1 fragment from which the reading frame of 820 amino acids is derived.

The sequence of the longest reading frame whose size is 820 amino acids is the SEQ ID NO: 2 sequence. This sequence is compared with that of the proteins contained in data banks.

In this sequence, there can be observed:

a-The existence of a homology with an enzyme of the *Erwinia chrysanthemi* species possessing an exo-poly-α-D-galacturonidase activity. This enzyme is described in J. Bacteriol. (1990), 172, pp. 4988–4995 and PNAS (1992), 83, pp. 8990–8994. The first document describes its sequence in detail.

b-The repetition of the sequence <<asparagine (Asn)-A-B-serine(Ser)>>, where A is isoleucine (Ile), leucine (Leu) or tyrosine (Tyr) and B valine (Val), isoleucine (Ile) or alanine (Ala), at positions 384–387,411–414, 433–436, 461–464, and 495–498. One of its sequences <<Asn-Ile-Ala-Ser>> in position 461–464 is part of a potential site of attachment of lipoproteins to lipids. This binding sequence is known in the literature (Hayashi S., Wu H. C. J. in Bioenerg. Biomembr., (1990), 22., pp. 451–471; Klein P., Somorjai R. L. Lau P. C. K., Protein Eng., (1988), 2, pp. 15–20; von Heijne G. in Protein Eng., (1989), 2, pp. 531–534; Mc Gavin M. J., Forsberg C. W., Crosby B., Bell A. W., Dignard D., Thomas D. Y. in J. Bacteriol. (1989), 171, pp. 5587–5595; Rothe B., Roggentio P., Frank R., Bloecker H., Schauer R., in J. Gen. Microbiol. (1989), 135, pp. 3087–3096).

According to a computer program contained in "UWGCG" (University Wiscousin Genetic Computer Group-University Research Park 575 Science Drive Suite B, Madisson Wis. 53711), a potential site for binding to lipids could be <<Asn Ile Ala Ser Asn Ile Leu Met Thr Gly Cys>>.

c-The presence of a highly positively charged sequence at the C-terminal end of the peptide sequence. It is the sequence <<Arg Arg Arg Val Lys Lys>> which is positioned at amino acids 804–809.

5-EXPRESSION OF VARIOUS FORMS OF THE GENE IN *ESCHERICHIA COLI* (K12)

Without additional experiment, neither the localization of the promoter responsible for the transcription of the gene nor the beginning of the messenger RNA encoding the protein can be determined with certainty. Consequently, it was chosen to express the proteins which start with a methionine, itself preceded by a ribosome-binding site also called Shine-Dalgarno sequence. The ribosome-binding site in *Escherichia coli* (K12) is described in the literature (PNAS (1974), 71 No. 4, pp. 1342–1346 and Nucleic Acid Research (1982), 10 No. 9, pp. 2971–2996).

The methionines which are preceded by a potential site for binding to the ribosomes are four in number and Table III shows their positions in the peptide sequence SEQ ID NO: 2 and the nucleotide sequences SEQ ID NO: 1.

TABLE III

| METHIONINE POSITION | SEQUENCES | |
|---|---|---|
| | PEPTIDE | NUCLEOTIDE |
| methionine 1 | 1 | 310-311-312 |
| methionine 2 | 112 | 642-643-644 |
| methionine 3 | 160 | 787-788-789 |
| methionine 4 | 194 | 888-889-890 |

5.1-Cloning into a vector for expressing the four proteins

A-Description of the polymerase chain reaction technique

The polymerase chain reaction (PCR) technique is a well known method which makes it possible to simultaneously copy the previously denatured strands for a DNA sequence using two oligonucleotides as primer [H. A. Erlich, "PCR Technology: Principles and Applications for DNA amplification", (1989), Ed. Macmillan Publishers Ltd, UK, and M. A. Innis et al., "PCR Protocols", (1990), Ed. Academic Press Inc San Diego, Calif. 92101, USA]. The principle of this technique is summarized below.

Numerous cycles, each of which consists of three stages, cause the amplification of the DNA strands of interest; the three stages are:

a) denaturation of the template b) annealing of the primers to the template c) extension of the primers.

After a few hours of cycles, hundreds of thousands of copies of the original template were produced by means of a thermostable DNA polymerase of *Thermus aquaticus*, usually called Taq polymerase. The PCR technique is based on the repetition of the three stages mentioned above.

a) Denaturation of the template:
  Double-stranded DNA is denatured into single-stranded DNA by incubating at high temperature (92° C.–96° C.) for approximately 2 minutes.

b) Annealing of the primers:
  These primers are a pair of synthetic oligonucleotides which anneal to the ends of the region to be amplified. The two primers anneal to opposite strands. The primers are added in excess so that the formation of the primer-template complex is favoured.

c) Extension of the primers:
  The stage during which Taq polymerase brings about the extension of the primer-template complex from 5' to 3' is carried out at 72° C.

In the PCR technique, the product of interest appears during the third cycle and it is then amplified substantially. During the progress of the cycles, the amplification product rapidly becomes the major template to which the primers become annealed.

B -Description of the primers used 5 synthetic oligonucleotides were prepared from the sequence of FIG. 1. The first oligonucleotide, called primer 1, whose sequence is the following (SEQ ID N° 3):

```
5'-GAT—CCA—TAT—GAC—GGT—CTC—AAC—CGA—AGT—TG-3'
|_____|  |_____|
    Region 1                Region 2
``` has two distinct regions. Region 1 is that which carries a cloning site CATATG corresponding to the endonuclease NdeI recognition site and region 2 that intended to become annealed to the 5' end of the gene encoding the protein starting with methionine 1.

The second oligonucleotide is the primer 2 whose sequence is the following (SEQ ID N° 4):

5'-GAT—CCA—TAT—GCT—GAT—CCA—GCG—ATG—TTT—TGG—GTG—G-3'
|_____|_____|
   Region 1                    Region 2 has two distinct regions. Region 1 is that which carries a cloning site CATATG corresponding to the endonuclease NdeI recognition site and region 2 which is intended to become annealed to the 5' end of the gene encoding the protein starting with methionine 2.

The third oligonucleotide constituting primer 3, whose sequence is the following (SEQ ID N° 5):

5'-GAT—CCA—TAT—GCG—TAA—TTA—TGT—CGA—TGC—TGC—AAT—CG-3'
|_____|_____|
   Region 1                    Region 2 has two distinct regions. Region 1 which carries a cloning site CATATG corresponding to the endonuclease NdeI recognition site and region 2 which is intended to become annealed to the 5' end of the gene encoding the protein starting with methionine 3.

The fourth oligonucleotide constitutes primer 4, whose sequence is the following (SEQ ID N° 6):

5'-GAT—CCA—TAT—GCG—TGA—TGG—TGT—CAG—CAT—TAA—GGA—TTT—TGG-3'
|_____|_____|
   Region 1                    Region 2 has two distinct regions. Region 1 is that which carries a cloning site CATATG corresponding to the endonuclease NdeI recognition site and region 2 intended to become annealed to the 3' end of the gene encoding the protein starting with methionine 4.

The fifth oligonucleotide called primer 5 whose sequence is the following (SEQ ID N° 7):

5'-GAT—CAA—GCT—TAT—CAA—TTC—CCT—GTT—AAT—TGC—AAA—AC-3'
|_____|_____|
   Region 1                    Region 2 has two distinct regions. Region 1 is that which carries a cloning site AAGCTT corresponding to the endonuclease HindIII recognition site and region 2 intended to become annealed to the 3' end of the gene encoding the protein.

5.2-Production of four amplified fragments corresponding to the four proteins 200 ng of the plasmid p838,7 hydrolysed with the restriction enzyme EcoRI (NEB) under the conditions recommended by the supplier, are mixed with:

100 ng of primer 1, 2, 3 or 4

100 ng of primer 5

200 μmol of each of the four deoxynucleotide triphosphates (adenosine, thymidine, cytidine, guanosine)

5 μl of reaction mixture concentrated ten fold (final concentration 67 mM Tris-HCl, pH 8.8, 16.6 mM $(NH_4)_2SO_4$, 1 mM β-mercaptophenol (6.7 mM EDTA, 0.15% Triton®, 200 mg of gelatin).

The volume is then adjusted to 50 μl by adding water.

0.5 μl, equivalent to 2.5 units of Taq polymerase (Beckman® ref. 267301) is then added. After homogenizing the solution, the reaction mixture is covered with paraffin oil in order to avoid evaporation of the aqueous solution during the polymerase chain reaction.

The amplification is performed over 18 reaction cycles of which the stages of a cycle are the following:

1 minute at 92° C.→denaturation 1 minute at 55° C.→annealing 3 minutes at 72° C.→polymerization After the 18 expected cycles, the enzymatic reaction is stopped by adding 20 mM EDTA.

The DNA fragments thus amplified have the expected sizes, which are the following:

primer 1: about 2460 bp primer 2: about 2130 bp primer 3: about 2000 bp primer 4: about 1880 bp These fragments are then isolated and purified on 1% agarose gel and then hydrolysed simultaneously with the enzymes NdeI and HindIII according to the recommendations of the supplier (New England Biolabs®) in order to form the NdeI and HindIII cohesive ends. After hydrolysis, the fragment is purified on an exclusion chromatography column.

5.3-Construction of the plasmids p868,26-p869,3-p886,3 and p887,7

This is the construction of the vectors for expressing the proteins whose corresponding peptide sequences start with the four potentially initial methionines described in Table III.

These four plasmids are prepared from the plasmid p466 corresponding to a vector for the cloning and expression of the complementary DNA, for *Aspergillus flavus* urate oxydase in *Escherichia coli*, described in Patent Appliction EP-0,408,461, which comprises a fragment of the plasmid pBR327 including the replication origin and the ampicillin-resistance gene, a synthetic *Escherichia coli* promoter, a Shine-Dalgarno sequence, followed by the gene encoding *Aspergillus flavus* urate oxydase flanked by the sequences recognized by the enzymes NdeI and HindIII, a transcriptional terminator (derived from the fd phage) and the lac i gene.

The plasmid p466 is hydrolysed according to the conditions recommended by the supplier with the enzymes NdeI and HindIII, and the fragment carrying the lac i gene, the fragment of the plasmid pBR327, the synthetic promoter, the Shine-Dalgarno sequence and the terminator is purified.

This fragment was ligated to each of the four fragments obtained after the polymerase chain reaction with the primers 1, 2, 3 and 4 in the presence of the primer 5 previously hydrolysed with the restriction endonucleases NdeI and HindIII in order to liberate the ends of these two sites, as described above (5.2). The product of these ligations was used to transform the strain RRI of *Escherichia coli* (K12) (GIBCO-BRL ref. 530–8261SA). The transformants obtained are analysed.

Table IV shows the transformants selected, corresponding to the various primers used in accordance with Table III, and Section 5.1, "B-description of the primers used".

TABLE IV

|  | CLONE | PLASMID |
| --- | --- | --- |
| PRIMER 1 | 868,26 | p868,26 |
| PRIMER 2 | 886,3 | p886,3 |
| PRIMER 3 | 887,7 | p887,7 |
| PRIMER 4 | 869,3 | p869,3 |

5.4-Analysis of the protein produced by each of the four clones

The general scheme for studying the expression in these four vectors was the following:

A colony is used to inoculate a test tube prefilled with LB medium supplemented with 100 µg/ml ampicillin. The test tube is then kept stirring overnight at 37° C.

From this preculture, a flask prefilled with the same LB medium is inoculated 1/100 and the incubation is continued under the same conditions. After culturing for one hour, the induction is caused by the addition of 1 mM IPTG (Sigma® I-9003) and the incubation is continued for 3 hours or 24 hours, still under the same temperature and stirring conditions. The cultures, after expression, are subjected to various manipulations:

a) Preparation of the bacterial pellets whose cell density corresponds to 0.2 ml at OD=1 ($\lambda$=600 nm) for analysis on SDS-PAGE 10% acrylamide or 1 ml OD=3 for biochemical assay of the eliminase activity.

b) Separation supernatant/bacterial pellet by centrifugation at 10000 revolutions/minute for 5 minutes at 4° C.

c) Osmotic shock. Osmotic shock is a technique commonly used for extracting the proteins contained in the periplasm of Gram-negative bacteria. This technique consists in causing bacteria to pass from a medium at high osmotic pressure into a medium at low osmotic pressure. For example Neu et al. in J. Biol. Chem., (1965) 240, pp. 3685–3692 recommend the use of a concentrated sucrose solution containing EDTA as medium at high osmotic pressure and water as medium at low osmotic pressure. In some specific cases, cytoplasmic enzymes which might be localized on the inner face of the cytoplasmic membrane could also be extracted by-this process Int. J. Biochem. (1979), 10, pp. 877–883).

Table V summarizes the results obtained on the various constructions.

TABLE V

| Methionine in position | Plasmid | Activity pellet | Activity supernatant | Activity osmotic shock |
| --- | --- | --- | --- | --- |
| 1 | p868,26 | + | + | + |
| 112 | p886,3 | + | + | + |
| 160 | p887,7 | + | − | not tested |
| 194 | p869,3 | + | − | not tested |

The plasmid p868,26, which produces in sufficient quantities the fragmentation enzyme in soluble form in the culture supernatant, is of specific interest for the production of fragments of predominantly 9–10 disaccharides.

5.5-Transformation of the plasmids p868,26 and p886,3 in the strains MC 1061 and TP 2339

The bacterial strain MC 1061 is described in J. Bacteriol. (1980), 143, No. 2, pp. 971–980, and the strain TP 2339 in U.S. Pat. No. 4,945,047.

Both bacterial strains were each transformed with the two plasmids p868,26 and p886,3 by the technique described in FMS (Sambrook Fritsch and Maniatis "Molecular cloning: A Laboratory manual" (1989), Ed. Cold Spring Harbor Press (N.Y.) 2nd edition pp. 1:75). Both transformed strains were cultured according to the method indicated above (5.4-analysis of the protein produced by each of the four clones). The bacterial pellets, the culture supernatants and the osmotic shock were assayed for their eliminase activity in the following manner:

the collected samples were diluted according to a series, and to each 125 µl of each dilution performed in the buffer A (described in 2.1-Incubation of the pools of transformed bacteria) are added 125 µl of high molecular mass N-acetylheparosan at the concentration of 20 g/l. The incubation is for 24 hours and the analysis of the fragments obtained is carried out according to the procedure described above (2.3-Analysis of the fragmentation products—Operating conditions for exclusion HPLC).

The results obtained are indicated in Table VI:

TABLE VI

|  | PELLET | | SUPERNATANT | | OSMOTIC SHOCK | |
|---|---|---|---|---|---|---|
|  | 3 hours | 24 hours | 3 hours | 24 hours | 3 hours | 24 hours |
| p868,26/MC 1061 | ND* | ND* | ND* | ND* | ND* | + |
| p868,26/TP2339 | ++ | + | ND* | +++ | ++ | ND* |
| p886,3/MC1061 | (+) | ND* | ND* | ND* | + | (+) |
| p886,3/TP2339 | ND* | ND* | ND* | ND* | ND* | ND* |

ND* = not detectable

In this table, it is observed that the strain TP 2339 transformed by the plasmid p868,26 (p868,26/TP2339) after incubating for 24 hours has a high activity in the culture supernatant.

6-PRODUCTION OF THE SOLUBLE RECOMBINANT ENZYME

6.1-Culture

To obtain the soluble recombinant enzyme, a culture of the recipient strain TP 2339, which is a strain RRI of *Escherichia coli* (K12) transformed by the plasmid p868,26, is performed under environmental conditions which are favourable to the formation of the enzyme.

The recombinant strain is stored in a 20% glycerol tube at the temperature of −80° C. The medium used is the C medium which is indicated in Table VII, the only difference being that yeast extract is added at the rate of 2 g/l initially and 10 g/l after 7 hours of culture. The fermenter used is an 18 liter MBR fermenter equipped with oxygen pressure, temperature and pH regulators and the like.
Preculture A tube of feed batch at −80° C. is thawed and 100 µl are collected and diluted 50 fold and then inoculated into a bottle with a low tube prefilled with 500 ml of LB medium. The bottle, containing a magnetic bar, is placed in a bath thermostatted at 30° C. and then connected to the fermenter to be inoculated via a hollow needle sterilely implanted in a septum. The plastic tube is inserted in a peristaltic pump and connected to a programmer. Following experiments and calculations, this scheme is convenient for inoculating a fermenter with an initial useful volume of 10 liters designed to start 11 hours after inoculating the bottle (for example, inoculation of the bottle started at 17 hours for inoculation of the fermenter at 4 o'clock in the morning).
Culture The culture parameters are the following:

pH 7.4

Oxygen pressure: 40 mmHg regulated by stirring.

Temperature: 37° C.

Excessive pressure 0.1 bar at the top of the fermenter.

Other reagents used during the culture are the following:

$H_2SO_4$ 3N consumption about 400 ml

KOH 3N consumption about 1200 ml

Antifoaming agent: Struktol® (Schill and Seilacher) type J 673®pure 50 ml.

A continuous supply of glucose is adjusted so as to provide a glucose concentration of between 10 and 20 g/l. The quantity of glucose consumed comprising the initial glucose of the medium is 1160 g.

The optical density of the solution measured at λ=600 nm reached the maximum of its value at a culture age of 11 hours, the biomass is then about 38 g/l.
Treatment of the culture suspension The suspension is vigorously centrifuged at 14000 g in pots. The supernatant contains the soluble recombinant enzyme. The supernatant can be directly used, after suitable dilution, to fragment the high molecular mass N-acetylheparosan. The supernatant can also be stored by freezing at −20° C.

6.2-Assay of the eliminase activity

The detection of the activity of the recombinant soluble eliminase was performed by the fragmentation caused by a quantity of high molecular mass N-acetylheparosan.

150 µl of purified high molecular mass N-acetylheparosan (Preparation) at 20 g/l, solubilized in pH 7.0 buffer, were used as substrate. (For the preparation of this buffer, dissolve 100 mmol of bis-Tris-propane and 200 mmol of NaCl in water, and adjust the pH to 7 with concentrated HCl and fill to 1 liter).

150 µl supernatant containing the soluble recombinant enzyme obtained as indicated above (6.1-Treatment of the culture suspension), at various dilutions performed in pH 7.0 buffer were added to this substrate. This mixture is homogenized by stirring and then incubated at 37° C. with stirring in a rotary shaker at 300 rpm.

The reading is performed after incubating for 24 hours and the measurement is expressed in eliminase unit (E.U.). One eliminase unit is defined as the quantity of activity necessary to fragment 0.1 mg of high molecular mass N-acetylheparosan at the concentration of 10 g/l into N-acetylheparosan of small molecular mass equal to 5000 Da, in 24 hours, at 37° C., at pH 7.0 in the presence of added 200 mM NaCl.

The analysis of the fragmented N-acetylheparosan is carried out by exclusion HPLC according to the conditions described in Section 2 (2.3-Analysis of the fragmentation products).
Calculations The soluble recombinant enzyme in the volume V (µl) diluted by a factor $d_E$ at an OD equal to 1 at λ=600 nm (this optical density for *Escherichia coli* (K5) corresponds to a biomass of 400 mg/l) at the end of culture $OD_E$ makes it possible to fragment the quantity $Q_{K5}$ (mg) of high molecular mass N-acetylheparosan.

The specific activity ($A_{SD}$) at the end of the culture of the soluble recombinant enzyme is obtained by the formula:

$$A_{SD} = \frac{10^3 \times d_E \times Q_{KS}(\text{mg}) \times 10}{V_E(\mu l) \times OD_E}$$

which gives EU values/ml at OD=1.

The eliminase activity of the soluble recombinant enzyme described above (6.1) is 10 E.U.

TABLE VII

| Composition and preparation of the medium C MEDIUM C | |
| --- | --- |
| Medium C is prepared by combining the three sterile solutions below: | |
| Solution No. 1 | |
| In 700 ml of ultra-purified water dissolve in order: | |
| Complexing agent: N'[Tris-(hydroxymethyl)methyl] glycine (Tricine marketed by Fluka ®) | 360 mg |
| FeSO$_4$.7H$_2$O | 280 mg |
| CaCl$_2$.2H$_2$O | 6.7 mg |
| MgCl$_2$.6H$_2$O | 1270 mg |
| K$_2$SO$_4$ | 8710 mg |
| NaCl | 500 mg |
| KCl | 5000 mg |
| Casein hydrolysate (main source of amino acids) HY CASE SF ® (marketed by Sheffield) | 25000 mg |
| Yeast extract (marketed by Difco ®) | 18000 mg |
| Solution of trace elements (cf. Table II) | 1 ml |
| Antifoaming agent Struktol J673 ® (marketed by Schill and Seilacher): a few drops using a Pasteur pipette. | |
| Adjust the pH to 7.4 with a KOH solution (d = 1.38) and fill to 850 ml with ultra-purified water. Autoclave the medium for 45 minutes at 120° C. | |
| Solution No. 2 | |
| In about 40 ml of ultra-purified water, dissolve 5 g of K$_2$HPO$_4$ and then adjust to 50 ml with the same solvent. Filter the solution obtained through a filter with a porosity of 0.2 μm. | |
| Solution No. 3 | |
| Dissolve 20.7 g of glucose in a sufficient quantity of ultra-purified water and adjust the volume to 100 ml with the same solvent. Autoclave at 110° C. for 30 minutes. | |

7-AMINO-TERMINAL SEQUENCE OF THE RECOMBINANT ENZYME

The strain RRI of *Escherichia coli* (K12) was transformed with the plasmid 868,26 and cultured as described above (6. Production of the soluble recombinant enzyme; 6.1 Culture).

The bacterial pellet recovered by centrifugation was placed for one hour in contact with a solution of Triton X-100 in order to extract the recombinant enzyme therefrom in a soluble form.

After two purification steps by anion exchange chromatography on DEAE Sepharose Fast Flow® and gel filtration on Superdex 200® (Pharmacia), a pool having the following characteristics was obtained:

0.26 mg/ml of total proteins eliminase activity on high MW N-acetylheparosan predominant band of about 70,000 Da in SDS PAGE This pool was dispatched for sequencing.

The sample of presumed recombinant enzyme was again loaded on a 10% SDS PAGE gel. The proteins were transferred onto Problot® membrane (Applied Biosystems) and stained with Coomassie blue. A doublet with a molecular mass close to 70,000 Da was detected.

The bands were loaded separately in an Applied Biosystems model 476 A sequencer. These two bands have the same amino-terminal sequence starting at threonine 2 (Thr2) residue of the theoretical peptide sequence SEQ ID NO: 2 of the recombinant enzyme.

The results obtained using an FSTNML program are given in Tables VIII and IX.

TABLE VIII

| Band No. 1 - SEQUENCE NUMBER: 112 | | | |
| --- | --- | --- | --- |
| Sequence cycles | HPLC*** | Identification | Conclusion |
| PTH-AA* No. 1 | Thr | 11 pm** | Thr |
| No. 2 | Val | 20 pm | Val |
| No. 3 | Ser | 4 pm | Ser |
| No. 4 | Thr | 6 pm | Thr |
| No. 5 | Glu | 6 pm | Glu |
| No. 6 | Val | 13 pm | Val |
| No. 7 | Asp | 5 pm | Asp |

TABLE IX

| SEQUENCE NUMBER: 113 | | | |
| --- | --- | --- | --- |
| Sequence cycles | HPLC*** | Identification | Conclusion |
| PTH-AA* No. 1 | Thr | 30 pm** | Thr |
| No. 2 | Val | 39 pm | Val |
| No. 3 | Ser | 33 pm | Ser |
| No. 4 | Thr | 14 pm | Thr |
| No. 5 | Glu | 29 pm | Glu |
| No. 6 | Val | 23 pm | Val |
| No. 7 | Asp | 22 pm | Asp |
| No. 8 | His | 10 pm | His |
| No. 9 | Asn | 29 pm | Asn |
| No. 10 | Glu | 15 pm | Glu |

*PTH-AA = phenylthiohydantoin
**pm = picomolar
***HPLC chromatographic conditions: reversed-phase chromatography; PTH C-18 ® column: (Biosystems); elution solvent gradient of (A) and (B): (A) = 30 mM acetate buffer in a 3.5% tetrahydrofuran solution (pH = 4) (B) = pure acetonitrile, gradient: 0–10 min B = 10%, 10–18 min B = 35–38%, 18–23 min B = 90%; flow rate = 0.3 ml/min; UV detection λ = 260 nm.

The amino-terminal sequence of the purified recombinant enzyme produced by the strain RRI of *Escherichia coli* (K12) transformed by the plasmid 868,26 corresponds to the beginning of the peptide sequence SEQ ID NO: 2 with the exception of amino-terminal formylmethionine. This amino acid was removed by an aminopeptidase (Waller J. P., J. Mol.Biol., (1963), 7, p483–496).

EXAMPLES

EXAMPLE 1

Fragmentation of high molecular mass N-acetylheparosan with the recombinant enzyme—production of an N-acetylheparosan with a molecular mass about 5000 Da 3 solutions (solutions A, B, C) of high molecular mass N-acetylheparosan are prepared (Preparation) by dissolving 20 g of N-acetylheparosan in ultra-purified water so as to obtain, after adding the recombinant enzyme solution, a final N-acetylheparosan concentration of 10 g/l. The soluble recombinant enzyme is used as enzyme. The quantity of soluble recombinant enzyme is calculated so that potentially, 15 g of high molecular mass N-acetylheparosan can be completely fragmented in 24 hours. The enzymatic reaction is carried out at 37° C. at pH 7 and with gentle stirring in the presence of 200 mM NaCl. The duration of the reaction is about 15 hours. It is monitored by exclusion HPLC as described in section 2.3 (2.3-Analysis of the fragmentation products—Operating conditions for exclusion HPLC). The reaction is stopped by cooling. 3 batches of small molecular mass N-acetylheparosan are thus obtained, batches A, B and C.

The 3 batches of small molecular mass N-acetylheparosan which are obtained at the end of the reaction have a predominant peak which corresponds to 4800 Da evaluated relative to a standard reference consisting of a heparin fraction with a molecular mass of 4800 Da. The proportion of high molecular mass fragments is negligible or even zero at the end of the enzymatic reaction.

---

We claim:

1. DNA fragment carrying a gene encoding an enzyme that fragments high molecular mass N-acetylheparosan and the expression systems permitting its biosynthesis, said DNA fragment having 3089 bp and corresponding to the nucleotide sequence SEQ ID N° 1.

2. DNA fragment encoding the peptide sequence SEQ ID N° 2.

3. DNA fragment encoding all or part of the peptide sequence SEQ ID N° 2.

4. Strain carrying a plasmid permitting the production of a recombinant enzyme that fragments high molecular mass N-acetylheparosan, said strain being obtained by transforming the strain RRI of *Escherichia coli* (K12) or another equivalent strain, with a vector carrying a DNA fragment corresponding to the sequence SEQ ID N° 1.

5. Strain deposited at the CNCM of the Institut Pasteur, Paris, France under the number 1-1352.

6. The strain TP 2339 transformed with the plasmid p868,26.

7. The plasmid p868,26.

* * * * *

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
    ( A ) LENGTH: 3089 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Escherichia coli
    ( B ) STRAIN: (K5) SEBR 3282

( x i ) SEQUENCE DESCRIPTION: SEQ ID NO: 1:

```
GATCCCGGAG  TAATTTCATC  AAGTGCGATC  CCTCCACCAG  TGACCTGACG  CCTCCCGGCG    60

TGTGAATCCT  TTCGGTAAAT  CCCTCTTCCA  GTGGATAGTG  ATACTGCTGC  ATCTTAATCT   120

TCTCCATGCA  ATAACTGTAT  ATTTATACAG  TAGCAAATAA  TTTGTTTGCT  ATCCAGCACG   180

TTTTGCAAAT  TACCTGAAAG  GTAATATCTA  TTCATATTCA  CAGTCTTTCT  ATCCATATAT   240

GGTTTTTTGG  GTAATAGAAT  AACCAGATAT  GCGGCGCAAC  GGGTGCTGCG  ACTATCTGGA   300

GATTTAACAT  GACGGTCTCA  ACCGAAGTTG  ACCACAACGA  ATACACAGGT  AACGGCGTTA   360

CGACATCATT  TCCGTATACC  TTCCGTATTT  TCAAAAAATC  CGACCTGGTT  GTTCAGGTGT   420

CTGACCTTAA  CGGTAACGTT  ACAAAACTAG  TGCTGGATGC  TGGTTATACG  GTAACAGGGG   480

CGGGAACTTA  TAGTGGCGGT  GCAGTGGTTC  TTCCGTCGCC  GCTTGCTGCT  GGCTGGCGAA   540

TCACGATAGA  GCGTGTGCTT  GATGTGGTGC  AGGAGACTGA  TCTTCGCAAT  CAGGGAAAAT   600

TTTTCCCCGA  AGTTCATGAG  GATGCATTTG  ACTACCTGAC  GATGCTGATC  CAGCGATGTT   660

TTGGGTGGTT  CAGACGTGCA  TTGATGAAAC  CATCTTTGCT  TGCAAAATAT  TACGATGCAA   720

AGCAAAACAG  AATATCTAAC  CTTGCCGATC  CATCACTTGA  GCAGGACGCT  GTAAATAATC   780

GCTCAATGCG  TAATTATGTC  GATGCTGCAA  TCGCCGGAGT  TATTGGTGGT  TTTGGTTGGT   840

TTATTCAGTA  TGGTTCTGGA  GCGGTATACA  GAACGTTCCA  GGATAAGATG  CGTGATGGTG   900

TCAGCATTAA  GGATTTTGGA  GCTCAAAATG  GAATCTTAAA  TGATAACAAG  GATGCTTTTA   960

CAAAATCATT  ACATTCGTTT  AGCAGTGTTT  TTGTTCCGGA  AGGGGTATTC  AATACATCTT  1020

TAGTTTCTCT  TTCACGTTGT  GGCTTGTACG  GAACAGGTGG  GGGAACGATA  AAACAGTATG  1080

ACAGAGATGG  TAATCATCTG  GTTTTTAACA  TGCCCGATGG  TGGCATGCTT  AGTACGCTAA  1140
```

| | | | | | |
|---|---|---|---|---|---|
|CAATTATGGG|AAATAAATCA|GATGATAGTG|TGCAGGGACA|CCAGGTGTCA|TTTTCAGGTG|1200|
|GCCATGATGT|ATCGGTTAAA|AATATCAGAT|TTACAAATAC|GCGAGGACCA|GGATTTAGCT|1260|
|TGATCGCTTA|TCCGGATAAT|GGTATTCCGT|CAGGTTACAT|TGTTAGAGAT|ATAAGAGGAG|1320|
|AGTATTTAGG|GTTCGCAAAT|AATAAAAAG|CAGGTTGTGT|GCTTTTGAT|TCATCGCAAA|1380|
|ATACGCTAAT|TGATGGTGTG|ATAGCCAGAA|ATTATCCTCA|GTTGGTGCA|GTGGAACTTA|1440|
|AAACAGCAGC|AAAATATAAC|ATTGTCAGCA|ATGTTATTGG|TGAAGAGTGT|CAGCACGTTG|1500|
|TTTACAATGG|AACTGAGACG|GAAACTGCCC|CAACGAATAA|TATCATTAGC|AGTGTAATGG|1560|
|CTAACAACCC|AAAATACGCC|GCAGTAGTTG|TTGGCAAGGG|GACTGGTAAC|CTGATTTCGG|1620|
|ATGTGCTGGT|TGATTACTCT|GAATCGGACG|CAAAGCAGGC|GCACGGCGTC|ACCGTTCAGG|1680|
|GAAATAATAA|TATTGCCAGT|AATATTCTAA|TGACTGGGTG|TGATGGGAAA|AATGAATCAG|1740|
|GAGATCTGCA|GACATCTACA|ACCATTCGTT|TCTTAGATGC|TGCACGCAGT|AATTATGCGT|1800|
|CAATATTCCC|CATGTATAGT|TCTTCCGGCG|TGGTTACCTT|CGAGGAAGGG|TGTATCAGGA|1860|
|ACTTTGTTGA|AATTAAACAT|CCGGGTGACA|GAAATAATAT|TCTGAGTTCT|GCATCAGCGG|1920|
|TGACTGGTAT|TTCCAGTATA|GACGGCACTA|CAAATAGCAA|TGTTGTTCAC|GTCCCTGCGC|1980|
|TTGGTCAGTA|CGTTGGGACT|ATGTCAGGGC|GTTTTGAATG|GTGGGTTAAA|TATTTTAACC|2040|
|TTGCTAACCA|GACGCTTGTT|TCTGCAGATA|AATTCAGAAT|GCTTGCTGAA|GGCGATGTAT|2100|
|CTCTGGCTGT|GGGAGGCGGT|ATAAGTTCGC|AATTGAAATT|ATTCAATAGT|GATAATACTA|2160|
|AAGGCACTAT|GTCGCTAATA|AATGGAAATA|TTCGAATATC|TACTGGAAAT|TCAGAATATA|2220|
|TACAGTTTTC|TGATTCAGCC|ATGACACCAT|CGACAACGAA|TACTTATTCT|CTTGGGTTGG|2280|
|CTGGTCGTGC|ATGGTCGGGG|GGATTTACCC|AGTCAGCGTT|TACGGTGCTG|TCCGATGCGC|2340|
|GTTTCAAGAC|TGCTCCAGAG|GTTATTGATG|AGAAAATACT|GGACGCATGG|GAAAGAGTGG|2400|
|AATGGGTTTC|ATACCAGTAC|CTTGACAGGA|TCGAAGTGAA|AGGTAAAGAC|GGAGCAAGAT|2460|
|GGCACTTTGG|TGCAGTTGCG|CAGCATGTTA|TCAGTGTATT|TCAGAATGAA|GGCATAGATG|2520|
|TGTCACGACT|GGCATTTATC|TGTTATGACA|AGTGGAATGA|GACCCCGGCA|GAATACAGGG|2580|
|ATGTGACGGA|AGAAGAGCAT|TCTGCAGGAG|TTTACCCACT|TATACAGACA|AAGGTTCTGG|2640|
|TACGCGAAGC|CGTCGAGGCT|GGTGAATGTT|ACGGTATCCG|TTATGAAGAG|GCTCTGATTC|2700|
|TGGAATCTGC|GATGATGAGA|CGCAGGGTTA|AAAAGCTGGA|AGAGCAAGTT|TTGCAATTAA|2760|
|CAGGGAATTG|AACCGTAAAT|GGTGTGTTGT|TGCGCGGTAT|ACTTTCCTG|AAGCAGGGTG|2820|
|TTTGCAAATA|AACGGGTTTC|GTTATGTCAT|TCCAACTAAC|CAATGAAACT|TCAAATCAGT|2880|
|GGCTTAGTGT|TAGTTCTCTT|GCTGCGGTTA|TTGCAGGTGT|CCCTCCGGAG|GTTGCTTTGG|2940|
|GGGCTTTGGC|TGGGGCGGTA|ATTTTGTTA|CCTCTGCGGT|AGAGTATCCT|ATTCGTCGTC|3000|
|GTGTACTCTT|GTCGATGCTT|AGCTTTCTCT|GCGGCCTTCT|TTTTTATAAA|CCAGCAGCAT|3060|
|CAATTCTTAT|CGGCATAGCC|AGCCTGATC|||||3089|

( 2 ) INFORMATION FOR SEQ ID NO: 2:

( i ) SEQUENCE CHARACTERISTICS:
        ( A ) LENGTH: 820 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

-continued

| | | | | | | | | | | | | | | |
|---|---|---|---|---|---|---|---|---|---|---|---|---|---|---|
| Met<br>1 | Thr | Val | Ser | Thr<br>5 | Glu | Val | Asp | His | Asn<br>10 | Glu | Tyr | Thr | Gly | Asn<br>15 | Gly |
| Val | Thr | Thr | Ser<br>20 | Phe | Pro | Tyr | Thr | Phe<br>25 | Arg | Ile | Phe | Lys | Lys<br>30 | Ser | Asp |
| Leu | Val | Val<br>35 | Gln | Val | Ser | Asp | Leu<br>40 | Asn | Gly | Asn | Val | Thr<br>45 | Lys | Leu | Val |
| Leu | Asp<br>50 | Ala | Gly | Tyr | Thr | Val<br>55 | Thr | Gly | Ala | Gly | Thr<br>60 | Tyr | Ser | Gly | Gly |
| Ala<br>65 | Val | Val | Leu | Pro | Ser<br>70 | Pro | Leu | Ala | Ala | Gly<br>75 | Trp | Arg | Ile | Thr | Ile<br>80 |
| Glu | Arg | Val | Leu | Asp<br>85 | Val | Val | Gln | Glu | Thr<br>90 | Asp | Leu | Arg | Asn | Gln<br>95 | Gly |
| Lys | Phe | Phe | Pro<br>100 | Glu | Val | His | Glu | Asp<br>105 | Ala | Phe | Asp | Tyr | Leu<br>110 | Thr | Met |
| Leu | Ile | Gln<br>115 | Arg | Cys | Phe | Gly | Trp<br>120 | Phe | Arg | Arg | Ala | Leu<br>125 | Met | Lys | Pro |
| Ser<br>130 | Leu | Leu | Ala | Lys | Tyr<br>135 | Tyr | Asp | Ala | Lys | Gln<br>140 | Asn | Arg | Ile | Ser | Asn |
| Leu<br>145 | Ala | Asp | Pro | Ser | Leu<br>150 | Glu | Gln | Asp | Ala | Val<br>155 | Asn | Asn | Arg | Ser | Met<br>160 |
| Arg | Asn | Tyr | Val | Asp<br>165 | Ala | Ala | Ile | Ala | Gly<br>170 | Val | Ile | Gly | Gly | Phe<br>175 | Gly |
| Trp | Phe | Ile | Gln<br>180 | Tyr | Gly | Ser | Gly | Ala<br>185 | Val | Tyr | Arg | Thr | Phe<br>190 | Gln | Asp |
| Lys | Met | Arg<br>195 | Asp | Gly | Val | Ser | Ile<br>200 | Lys | Asp | Phe | Gly | Ala<br>205 | Gln | Asn | Gly |
| Ile | Leu<br>210 | Asn | Asp | Asn | Lys | Asp<br>215 | Ala | Phe | Thr | Lys | Ser<br>220 | Leu | His | Ser | Phe |
| Ser<br>225 | Ser | Val | Phe | Val | Pro<br>230 | Glu | Gly | Val | Phe | Asn<br>235 | Thr | Ser | Leu | Val | Ser<br>240 |
| Leu | Ser | Arg | Cys | Gly<br>245 | Leu | Tyr | Gly | Thr | Gly<br>250 | Gly | Gly | Thr | Ile | Lys<br>255 | Gln |
| Tyr | Asp | Arg | Asp<br>260 | Gly | Asn | His | Leu | Val<br>265 | Phe | Asn | Met | Pro | Asp<br>270 | Gly | Gly |
| Met | Leu | Ser<br>275 | Thr | Leu | Thr | Ile | Met<br>280 | Gly | Asn | Lys | Ser | Asp<br>285 | Asp | Ser | Val |
| Gln | Gly<br>290 | His | Gln | Val | Ser | Phe<br>295 | Ser | Gly | Gly | His | Asp<br>300 | Val | Ser | Val | Lys |
| Asn<br>305 | Ile | Arg | Phe | Thr | Asn<br>310 | Thr | Arg | Gly | Pro | Gly<br>315 | Phe | Ser | Leu | Ile | Ala<br>320 |
| Tyr | Pro | Asp | Asn | Gly<br>325 | Ile | Pro | Ser | Gly | Tyr<br>330 | Ile | Val | Arg | Asp | Ile<br>335 | Arg |
| Gly | Glu | Tyr | Leu<br>340 | Gly | Phe | Ala | Asn | Asn<br>345 | Lys | Lys | Ala | Gly | Cys<br>350 | Val | Leu |
| Phe | Asp | Ser<br>355 | Ser | Gln | Asn | Thr | Leu<br>360 | Ile | Asp | Gly | Val | Ile<br>365 | Ala | Arg | Asn |
| Tyr | Pro<br>370 | Gln | Phe | Gly | Ala | Val<br>375 | Glu | Leu | Lys | Thr | Ala<br>380 | Ala | Lys | Tyr | Asn |
| Ile<br>385 | Val | Ser | Asn | Val | Ile<br>390 | Gly | Glu | Glu | Cys | Gln<br>395 | His | Val | Val | Tyr | Asn<br>400 |
| Gly | Thr | Glu | Thr | Glu<br>405 | Thr | Ala | Pro | Thr | Asn<br>410 | Asn | Ile | Ile | Ser | Ser<br>415 | Val |

```
Met Ala Asn Asn Pro Lys Tyr Ala Ala Val Val Val Gly Lys Gly Thr
        420             425                 430
Gly Asn Leu Ile Ser Asp Val Leu Val Asp Tyr Ser Glu Ser Asp Ala
        435             440                 445
Lys Gln Ala His Gly Val Thr Val Gln Gly Asn Asn Ile Ala Ser
    450             455                 460
Asn Ile Leu Met Thr Gly Cys Asp Gly Lys Asn Glu Ser Gly Asp Leu
465             470                 475                     480
Gln Thr Ser Thr Thr Ile Arg Phe Leu Asp Ala Ala Arg Ser Asn Tyr
            485                 490                 495
Ala Ser Ile Phe Pro Met Tyr Ser Ser Gly Val Val Thr Phe Glu
            500             505                 510
Glu Gly Cys Ile Arg Asn Phe Val Glu Ile Lys His Pro Gly Asp Arg
        515             520                 525
Asn Asn Ile Leu Ser Ser Ala Ser Ala Val Thr Gly Ile Ser Ser Ile
        530             535                 540
Asp Gly Thr Thr Asn Ser Asn Val Val His Val Pro Ala Leu Gly Gln
545             550                 555                     560
Tyr Val Gly Thr Met Ser Gly Arg Phe Glu Trp Trp Val Lys Tyr Phe
                565             570                 575
Asn Leu Ala Asn Gln Thr Leu Val Ser Ala Asp Lys Phe Arg Met Leu
            580                 585                 590
Ala Glu Gly Asp Val Ser Leu Ala Val Gly Gly Gly Ile Ser Ser Gln
        595             600                 605
Leu Lys Leu Phe Asn Ser Asp Asn Thr Lys Gly Thr Met Ser Leu Ile
    610             615                 620
Asn Gly Asn Ile Arg Ile Ser Thr Gly Asn Ser Glu Tyr Ile Gln Phe
625             630                 635                     640
Ser Asp Ser Ala Met Thr Pro Ser Thr Thr Asn Thr Tyr Ser Leu Gly
            645                 650                 655
Leu Ala Gly Arg Ala Trp Ser Gly Gly Phe Thr Gln Ser Ala Phe Thr
        660             665                 670
Val Leu Ser Asp Ala Arg Phe Lys Thr Ala Pro Glu Val Ile Asp Glu
        675             680                 685
Lys Ile Leu Asp Ala Trp Glu Arg Val Glu Trp Val Ser Tyr Gln Tyr
    690             695                 700
Leu Asp Arg Ile Glu Val Lys Gly Lys Asp Gly Ala Arg Trp His Phe
705             710                 715                     720
Gly Ala Val Ala Gln His Val Ile Ser Val Phe Gln Asn Glu Gly Ile
            725                 730                 735
Asp Val Ser Arg Leu Ala Phe Ile Cys Tyr Asp Lys Trp Asn Glu Thr
            740                 745                 750
Pro Ala Glu Tyr Arg Asp Val Thr Glu Glu His Ser Ala Gly Val
        755             760                 765
Tyr Pro Leu Ile Gln Thr Lys Val Leu Val Arg Glu Ala Val Glu Ala
    770             775                 780
Gly Glu Cys Tyr Gly Ile Arg Tyr Glu Glu Ala Leu Ile Leu Glu Ser
785             790                 795                     800
Ala Met Met Arg Arg Arg Val Lys Lys Leu Glu Glu Gln Val Leu Gln
            805                 810                 815
Leu Thr Gly Asn
        820
```

( 2 ) INFORMATION FOR SEQ ID NO: 3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO: 3:

GATCCATATG ACGGTCTCAA CCGAAGTTG         29

( 2 ) INFORMATION FOR SEQ ID NO: 4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO: 4:

GATCCATATG CTGATCCAGC GATGTTTGG GTGG         34

( 2 ) INFORMATION FOR SEQ ID NO: 5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO: 5:

GATCCATATG CGTAATTATG TCGATGCTGC AATCG         35

( 2 ) INFORMATION FOR SEQ ID NO: 6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO: 6:

GATCCATATG CGTGATGGTG TCAGCATTAA GGATTTTGG         39

( 2 ) INFORMATION FOR SEQ ID NO: 7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO: 7:

GATCAAGCTT ATCAATTCCC TGTTAATTGC AAAAC         35